United States Patent
Perrin et al.

(10) Patent No.: US 8,574,546 B2
(45) Date of Patent: Nov. 5, 2013

(54) SUBSTITUTED ARYL-FLUOROBORATES AS IMAGING AGENTS

(75) Inventors: David Perrin, Vancouver (CA); Richard Ting, Vancouver (CA); Christopher Overall, Vancouver (CA)

(73) Assignee: The University of British Columbia, Vancouver (CA)

( * ) Notice: Subject to any disclaimer, the term of this patent is extended or adjusted under 35 U.S.C. 154(b) by 588 days.

(21) Appl. No.: 12/670,108

(22) PCT Filed: Jul. 24, 2008

(86) PCT No.: PCT/CA2008/001368
§ 371 (c)(1),
(2), (4) Date: Jun. 22, 2010

(87) PCT Pub. No.: WO2009/012596
PCT Pub. Date: Jan. 29, 2009

(65) Prior Publication Data
US 2010/0254903 A1    Oct. 7, 2010

Related U.S. Application Data

(60) Provisional application No. 60/935,038, filed on Jul. 24, 2007.

(51) Int. Cl.
*A61K 51/04* (2006.01)

(52) U.S. Cl.
USPC ....... 424/1.89; 424/1.65; 424/1.69; 424/1.73; 424/9.3

(58) Field of Classification Search
USPC ........... 424/1.65, 1.69, 1.89, 1.45, 1.57, 1.73, 424/9.3; 562/7; 548/302.7, 303.7, 304.1
See application file for complete search history.

(56) References Cited

U.S. PATENT DOCUMENTS

2006/0128664 A1 *  6/2006  Holmes-Farley et al. ...... 514/64

FOREIGN PATENT DOCUMENTS

| WO | 2005077967 | | 8/2005 |
|---|---|---|---|
| WO | WO-2005/077967 | * | 8/2005 |

OTHER PUBLICATIONS

Harwig et al., "Synthesis and characterization of 2,6-difluoro-4-carboxyphenylboronic acid and a biotin derivative thereof as captors of anionic aqueous [18F]-fluoride for the preparation of [18F/19F]-labeled aryltrifluoroborates with high kinectic stability"; Tehtrahedron Letters 49 (2008) 3152-3156.
Li et al., "Hydrolytic stability of nitrogenous-heteroaryltrifluoroborates under aqueous conditions at near neutral pH"; Journal of Fluorine Chemistry 130 (2009) 377-382.
Ting et al., "Arylfluoroborates and Alkylfluorosilicates as Potential PET Imaging Agents: High-Yielding Aqueous Biomolectular 18F-Labeling"; J. Am. Chem. Soc. (2005) 127, 13094-13095.
Ting et al., "Capturing aqueous [18F]-fluoride with an arylboronic ester for PET: Synthesis and aqueous stability of a fluorescent [18F]-labeled aryltrifluoroborate"; Journal of Fluorine Chemistry 129 (2008) 349-358.
Ting et al., "Toward [18F]-Labeled Aryltrifluoroborate Radiotracers: In Vivo Positron Emission Tomography Imaging of Stable Aryltrifluoroborate Clearance in Mice"; J. Am. Chem. Soc. (2008) 130, 12045-12055.
Ting et al., "Substituent Effects on Aryltrifluoroborate Solvolysis in Water: Implications for Suzuki-Miyaura Coupling and the Design of Stable 18F-Labeled Aryltrifluoroborates for Use in PET Imaging"; J. Org. Chem. (2008) 73, 4662-4670.
International Preliminary Report on Patentability for PCT/CA2008/001368 mailed on Feb. 4, 2010.

* cited by examiner

*Primary Examiner* — Michael G. Hartley
*Assistant Examiner* — Jagadishwar Samala
(74) *Attorney, Agent, or Firm* — Carol L. Francis; Rudy J. Ng; Bozicevic, Field & Francis LLP

(57) ABSTRACT

Substituted aryl-boron compounds comprising at least one $^{18}F$ atom, as illustrated by the formula (I), where at least one of $Y^1$ or $Y^2$ is $^{18}F$ and $A^1$ is a substituted aromatic ring, with $G^{1-5}$ being, independently, C or N, and where the substitutents of the aromatic ring or polycyclic moiety (other than boron) comprise at least one electron-withdrawing group (EWG), providing that sigma total ($\sigma_{total}$) for all substituents on the aromatic ring or polycyclic moiety except B is about 0.06 or more when said at least one EWG is positioned ortho to B, or about 0.2 or more when no EWG is positioned ortho to B. The compounds include neutral (N=1) and ionic borate (N=2) embodiments. The compounds are useful as positron emission tomography (PET) imaging agents.

(I)

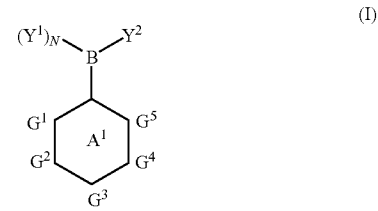

42 Claims, 5 Drawing Sheets

SUBSTITUTED ARYL-FLUOROBORATES AS IMAGING AGENTS

RELATED APPLICATIONS

This application claims priority from U.S. patent application No. 60/935,038 filed Jul. 24, 2007, the contents of which are hereby incorporated by reference.

FIELD OF INVENTION

This invention relates to the field of $^{18}F$ radiolabeled reagents for use in positron emission tomography (PET) imaging.

BACKGROUND OF THE INVENTION $^{18}F$ is the isotope of choice for many PET cancer imaging applications. It is a positron emitter having (i) a low trajectory energy (0.635 MeV), which allows for good signal resolution, (ii) a moderate half-life (~110 minutes) and, (iii) is readily generated in a cyclotron from the stable element, $^{19}F$.

PET imaging agents are often based on a labeled biomolecule. An example is fluorodeoxyglucose (FDG). Since the high energy particle bombardment used to produce $^{18}F$ will destroy complex organic molecules, $^{18}F$ is first made as a fluoride in a cyclotron and subsequently attached to a biomolecule to be used as the imaging agent. Also, conditions used to incorporate $^{18}F$ into other molecules are often too harsh for direct labeling of a biomolecule. Therefore, $^{18}F$ is usually introduced into a precursor (such as an arylfluoride) that is then subsequently appended to a larger molecule. Such multi-step procedures result in delay from initial isotope production to use of a particular imaging agent with consequent loss in specific radioactivity.

PCT Application published as WO 2005/0077967 summarizes some of the known methodologies for incorporating $^{18}F$ into imaging agents and describes a new approach which makes use of boron or silicon as acceptors capable of binding several $^{18}F$ atoms, thus increasing the density of positron emitters in the resulting imaging agent. Also, the use of boronic acids/esters as an $^{18}F$ acceptor circumvented the previous practice of generating arylfluorides in multi-step procedures.

SUMMARY OF THE INVENTION

In addition to isotope half-life, another consideration in the design of PET imaging agents is the longevity of the agent itself. As part of this consideration, it is desirable that the imaging agent be sufficiently stable with respect to loss of $^{18}F$ atoms from the agent (termed herein "de-18-fluorination"). In some applications it is desirable for the imaging agent to have a half-life with respect to de-18-fluorination of up to 60 minutes or more.

The invention described herein is based, in part, on the discovery that particular substituted arylboronic acid/esters used as captors of aqueous fluoride can be converted to arylfluoroborates which can function as PET imaging agents and exhibit enhanced resistance to de-18-fluorination. Surprisingly, aryl moieties selected so that their substituents contribute to an overall electron withdrawing effect, permit the resulting fluoroborate to resist defluorination. Half-lives with regard to de-18-fluorination of the resulting arylfluoroborates may be at least about 15 minutes or more; at least about 20 minutes or more; at least about 30 minutes or more; at least about 40 minutes or more; at least about 50 minutes or more; or at least about 60 minutes or more. Half-lives of multiple hours (e.g. 180 minutes, 300 minutes, etc.) can also be obtained.

In some applications where loss of fluorine is desired (e.g. comparison of externally bound ligand that loses fluoride to the surrounding bone to internalized ligands that keep the fluoride in a targeted cell) shorter half-lives may be desirable. However, for whole body imaging, longer half-lives are desirable.

One aspect of the invention makes use of a positron emitting compound or salt thereof wherein the compound has the formula:

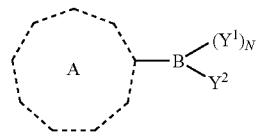

wherein:
B is boron;
A is a single substituted aromatic ring or an aromatic ring joined to one or more additional rings to form a substituted polycyclic moiety, wherein ring atoms comprise carbon and optionally, one or more heteroatoms, and substituents of the aromatic ring or polycyclic moiety other than B comprise at least one electron-withdrawing group (EWG);
each $(Y^1)_n$ is independently selected from the group consisting of $R^1$, $^{18}F$ and $^{19}F$, and n=1 or 2;
$Y^2$ is selected from the group consisting of $R^1$, $^{18}F$ and $^{19}F$;
$R^1$ is a non-interfering substituent with regard to fluorination of B;
providing that at least one of $(Y^1)_n$ and $Y^2$ is $^{18}F$;
providing that $\sigma_{total}$ for all substituents on the aromatic ring or polycyclic moiety except B is about 0.06 or more when said at least one EWG is positioned ortho to B, or about 0.2 or more when no EWG is positioned ortho to B;
and providing that said at least one EWG is not a single bromomethyl group positioned ortho to B.

In the aforementioned formula, the optional ring heteroatoms may be nitrogen (N), phosphorous (P) or boron (B). Exclusion of embodiments where the only EWG is a single bromomethyl group ortho to B avoids compounds disclosed in WO 2005/077967 as intermediates in the preparation of a phenyl boronic acid/ester conjugate of folate.

The compound may have the formula:

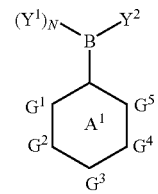

wherein:
$A^1$ is the aromatic ring and $G^{1-5}$ are independently substituted or unsubstituted C or N;
$G^1$ with $G^2$, $G^2$ with $G^3$, $G^3$ with $G^4$ or $G^4$ with $G^5$ optionally join with substituents thereof to form an additional ring or rings (e.g. two rings) of said polycyclic moiety;

and wherein at least one of $G^{1-5}$ or at least one of said additional ring or rings is substituted by said at least one EWG.

Another aspect of this invention is a method of making a positron emitting compound or salt thereof, comprising contacting an $^{18}F$ source with a compound or salt thereof, when the compound has the formula:

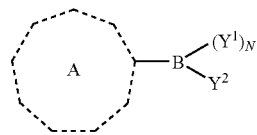

wherein:
B is boron;
A is a single substituted aromatic ring or an aromatic ring joined to one or more additional rings to form a substituted polycyclic moiety, wherein ring atoms comprise carbon and optionally, one or more heteroatoms, and substituents of the aromatic ring or polycyclic moiety other than B comprise at least one electron-withdrawing group (EWG);
n is 1 or 2, each $(Y^1)_n$ and $Y^2$ are independently selected from the group consisting of $R^1$ and a leaving group that can be displaced by fluoride, and at least one of $(Y^1)_n$ and $Y^2$ is said leaving group;
$R^1$ is a non-interfering substituent with regard to fluorination of B;
and wherein $\sigma_{total}$ for all substituents on the aromatic ring or polycyclic moiety except B is about 0.06 or more when said at least one EWG is positioned ortho to B, or about 0.2 or more when no EWG is positioned ortho to B, and further providing that the at least one EWG is not a single bromomethyl group positioned ortho to B.

Another aspect of this invention is a method of performing PET imaging comprising administering an imaging effective amount of a positron emitting compound or salt of this invention to a subject or object to be subjected to PET.

Another aspect of this invention is a method of selecting a PET imaging agent or precursor thereof having resistance to de-18-fluorination, comprising:
(i) providing one or more compounds or salts thereof of the formula:

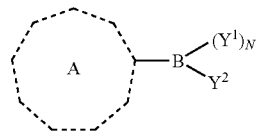

wherein:
B is boron;
A is a single substituted aromatic ring or an aromatic ring joined to one or more additional rings to form a polycyclic moiety, wherein ring atoms comprise carbon and optionally, one or more heteroatoms, and substituents of the aromatic ring or polycyclic moiety other than B comprise at least one electron-withdrawing group (EWG);
each $(Y^1)_n$ is independently selected from the group consisting of $R^1$ and fluorine and n=1 or 2;
$Y^2$ is selected from the group consisting of $R^1$ and fluorine;
$R^1$ is a non-interfering substituent with regard to fluorination of B;
providing that at least one of $(Y^1)_n$ and $Y^2$ is fluorine;
providing that $\sigma_{total}$ for all substituents on the aromatic ring or polycyclic moiety except B is about 0.06 or more when said at least one EWG is positioned ortho to B, or about 0.2 or more when no EWG is positioned ortho to B;
and further providing that said at least one EWG is not a single bromomethyl group positioned ortho to B; and
(ii) assessing half-life of the presence of the fluorine bound to B; and
(iii) selecting a compound or compounds having said half-life of about 30 minutes or more as said imaging agent or precursor thereof.

Another aspect of this invention is the use of a positron emitting compound or salt of this invention as a PET imaging agent.

Another aspect of this invention is the use of a compound as described above in the manufacture of an $^{18}F$ containing PET imaging agent or precursor thereof.

In particular embodiments, the compound may be of Formula 1:

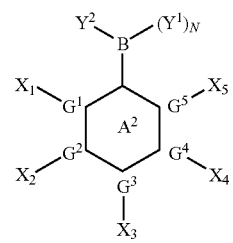

Formula 1 wherein:
ring $A^2$ is aromatic;
$G^1$, $G^2$, $G^3$, $G^4$ and $G^5$ are independently substituted or unsubstituted carbon or a heteroatom;
$X^1$, $X^2$, $X^3$, $X^4$, and $X^5$ are each: H or R, or is absent when the ring atom to which it is attached is unsubstituted N, further providing that one or two additional rings may be formed from $X^1$ and $X^2$, $X^2$ and $X^3$, $X^3$ and $X^4$, or $X^4$ and $X^5$, and with the proviso that at least one of $X^{1-5}$ or a substituent on an additional ring is an electron withdrawing group (EWG);
n is 1 or 2, each $Y^1$ is independently selected from the group consisting of:
$R^1$, $^{18}F$, and a leaving group (including $^{19}F$) that can be displaced by fluoride; and
$Y^2$ is $R^1$, $^{18}F$ or a leaving group (including $^{19}F$) that can be displaced by fluoride; or
$Y^1$ and $Y^2$ together form a single leaving group that can be displaced by fluoride. One or more counterions may be present when the compound is charged.

R may be selected for a desired property such as being a linking group, a biomolecule for imaging purposes or a combination of a linking group and such a biomolecule or any non-interfering group, including an optionally substituted, saturated or unsaturated, linear, branched or cyclic alkyl group of 1 to 15 carbon atoms such as methyl or an optionally substituted aryl group. In particular embodiments, at least one of $X^1$, $X^2$, $X^3$, $X^4$, and $X^5$, or at least one of $X^2$, $X^3$, and $X^4$, is a linking group.

$R^1$ may be any non-interfering group with regard to fluorination of B, such as an optionally substituted, saturated or unsaturated, linear, branched or cyclic alkyl group of 1 to 15 carbon atoms (such as methyl) or an optionally substituted aryl group.

$R^1$ may be absent (i.e., n=0 in Formula 2) and when present, each $R^1$ may be independently, an optionally substituted aryl group or an optionally substituted, linear, branched or cyclic, saturated or unsaturated alkyl group of 1 to 15 carbon atoms. In particular embodiments, each $R^1$ may be independently a 1 to 15 carbon optionally substituted saturated or unsaturated, linear, branched or cyclic alkyl group. In particular embodiments, $R^1$ is independently a 1 to 5 carbon, saturated or unsaturated, linear, branched or cyclic alkyl group. $R^1$ may contain other atoms such as nitrogen at or near the attachment point to B.

In certain embodiments such as where a particular G atom (e.g. $G''$) is a nitrogen or phosphorous atom, the associated X group (e.g. $X''$) is either absent or may be H, or a linear, branched or cyclic, saturated or unsaturated alkyl group of carbon atoms that is bound to the nitrogen. A particular example is methyl. When $X''$ is present in the form of a dissociable proton, or as a stable N-alkyl or N-aryl, it is recognized that the $G''$ nitrogen atom will be positively charged.

In some embodiments, the sum of sigma values for $X^1$, $X^2$, $X^3$, $X^4$, and $X^5$ will be about 0.06 or more. In other embodiments the sum may be greater than or equal to about 0.12, 0.15, 0.20, 0.25, 0.30, 0.35, 0.5, 0.6, 0.8, 1.0 or 1.15. In some embodiments, neither $X^1$ and $X^5$ (when present and not hydrogen) are capable of anchimerically assisting defluorination of the boron atom. In particular embodiments, at least one of $X^1$ and $X^5$ is an electron-withdrawing group (EWG) and the sum of the sigma values are not be lower than a value of about 0.06.

In particular embodiments of the present invention, each of $G^1$, $G^2$, $G^3$, $G^4$, and $G^5$ is a carbon atom (such as is the case with Formula 2) in which case the definitions of $X^{1-5}$ and $R^1$ are as noted above.

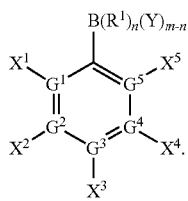

Formula 2

In accordance with another aspect, this invention makes use of the aforementioned arylfluoroborates, wherein one or more of $Y^1$ and $Y^2$ (or Y in Formula 2) is an $^{18}F$ atom, for use as an imaging agent or as a precursor of an imaging agent. In Formula 2, when m=3 and n is 0, 1, or 2, the boron atom (B) has a formal negative charge. It is recognized that in some cases, m=2 and n is 0 or 1, in which cases the boron has an empty p-orbital and is not formally charged. In the latter case, an additional ligand may be added such that m=3 and n is 0, 1, or 2 as noted above. It is recognized that for boronic acids, esters and diamine adducts, m is usually 2 and n is 0, or 1.

This invention also provides a method of making a precursor compound which comprises converting a corresponding arylboronic acid variant of any of the aforementioned compounds to an arylboronic ester, wherein one or both of $Y^1$ and $Y^2$ or Y is a leaving group displaceable by fluoride. This invention also provides a method of making a $^{18}F$ containing compound which comprises replacing at least one of said leaving group or groups of the aforesaid arylboronic ester with $^{18}F$.

Methods of this invention make use of substituted arylboronyl compounds, wherein $Y^1$, $Y^2$ or Y is a moiety that can be displaced by reaction with fluoride. These may be used as precursor molecules to the above-described $^{18}F$ labeled arylfluoroborate compounds by reaction with a suitable source of $^{18}F$. In this aspect of the invention, Y may (for example) be an alkoxy, halide, amine (e.g. alkyl, aryl), or thiol (alkyl, aryl) moiety.

Examples of electron-withdrawing groups include but are not limited to: F, Cl, Br or I, —C=O, —C≡N, —$SO_2$R, —$NO_2$, —RC=NR, —N=$CR_2$, —$N^+R$=$CR_2$, —COON, —COOR, —$CONH_2$, —CONHR, —$CONR_2$, —CHO, —COR, —$CO_2$OR, —NO, and α-haloalkyl groups such as —$CF_3$, —$CCl_3$, —$CF_2$R, and $CCl_2$R (when R is alkyl or aryl). In particular embodiments, the electron-withdrawing group at a particular position may be selected to take account of its inductive and mesomeric character and also, when in an ortho position, its inability to anchimerically assist the loss of fluorine from the boron atom, as described below.

In accordance with another aspect of the invention, at least one of $X^1$, $X^2$, $X^3$, $X^4$, $X^5$ is configured so as to allow conjugation to a biomolecule. In accordance with another aspect of the invention are compounds of Formulas 1 and 2 wherein at least one of $X^1$-$X^5$ is a linking group and may further be joined to (or be) a biomolecule for use in imaging applications. In accordance with another aspect of the invention, at least one of $X^1$, $X^2$, $X^3$, $X^4$, $X^5$ is conjugated to a biomolecule.

In accordance with another aspect of the invention, at least one of $X^1$ and $X^5$ is not H when $G^1$, $G^2$, $G^3$, $G^4$, and $G^5$ are exclusively carbon.

In accordance with another aspect of the invention, at least one of $X^1$ and $X^5$ is F, Cl, Br, $CF_3$, $CCl_3$, I, CN, $CF_2$—R, $CCl_2$—R, $CBr_3$, $CBr_2$-R, $OCHF_2$, $OCF_3$, NC or N$(CH_3)_3$ (wherein R is alkyl or aryl).

When $X^1$ and/or $X^5$ are not H, it is desirable that neither be a group that can anchimerically or protolytically assist the defluorination of the neighboring fluoroborate group. In this aspect of the invention, neither $X^1$ nor $X^5$ is —$NO_2$, —C(O)R, —C(O)$NR_2$, C(O)OR, C(O)$NH_2$, C(O)NHR, C(O)SR, $SO_2$NH, $SO_2NR_2$, $SO_2$C (wherein R is alkyl or aryl).

In accordance with another aspect of the invention, 1 or 2 of $X^1$ and $X^2$, $X^2$ and $X^3$, $X^3$ and $X^4$ or $X^4$ and $X^5$ of Formula 1 or 2 are linked to form one or two additional rings. These rings may be unsaturated and may comprise at least one substituent electron-withdrawing group. In either case, the ring may be a suitably substituted naphthalene, a quinoline or a heterocycle.

A further aspect of the invention are methods for selections or screening substituted aryl fluoroborate compounds, for their ability to resist defluorination as an indicator of their longevity as a radio imaging agent for PET. Various methods may be employed such as described below.

Other aspects and features of the present invention will become apparent to those ordinarily skilled in the art upon review of the following description of specific embodiments of the invention in conjunction with the accompanying figures.

DETAILED DESCRIPTION

Figure 1:
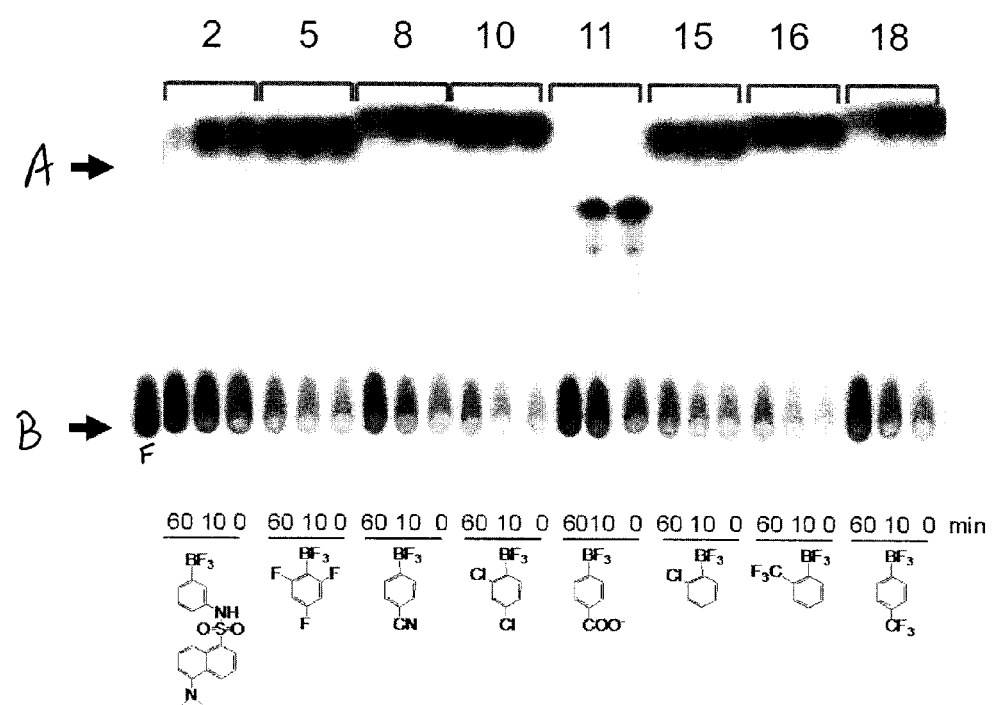
FIG. 1: shows an autoradiograph of a silica thin-layer chromatogram of various $^{18}F$-fluorinated compounds, demonstrating the relative amount of dissociation of the $^{18}F$ label from certain compounds at 0, 10 and 60 minutes after labeling. "F" indicates free fluorine from a 'dummy' reaction as a negative control. Line A indicates the $^{18}$F labeled compounds. Line B is the baseline.
Figure 2:
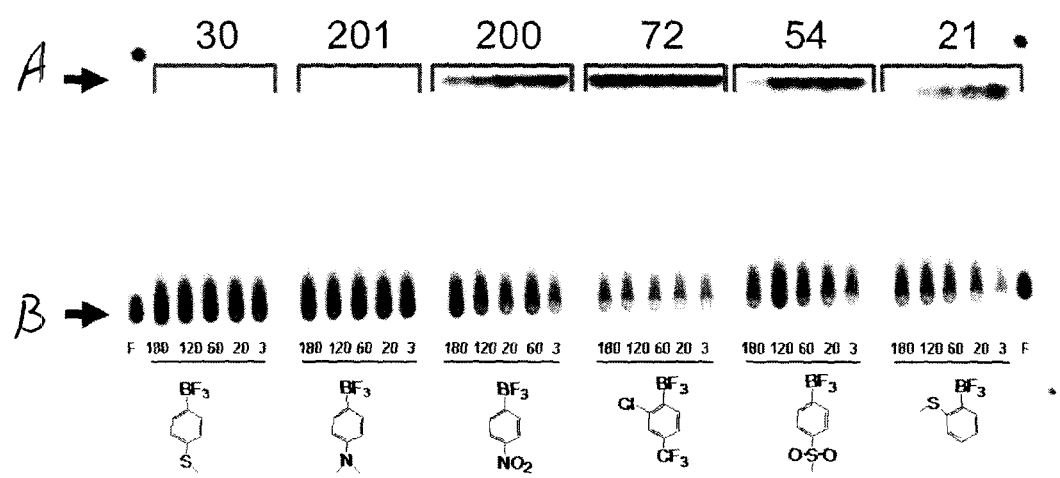
FIGS. 2, 3 and 4: show autoradiographs of silica thin-layer chromatograms of various $^{18}$F-fluorinated compounds, demonstrating the relative amount of dissociation of the $^{18}$F label from certain compounds at 3, 20, 60, 120, and 180 minutes after labeling. "F" indicates the free fluorine from a 'dummy' reaction as a negative control. Line A indicates the $^{18}$F labeled compounds. Line B is the baseline.
Figure 3:
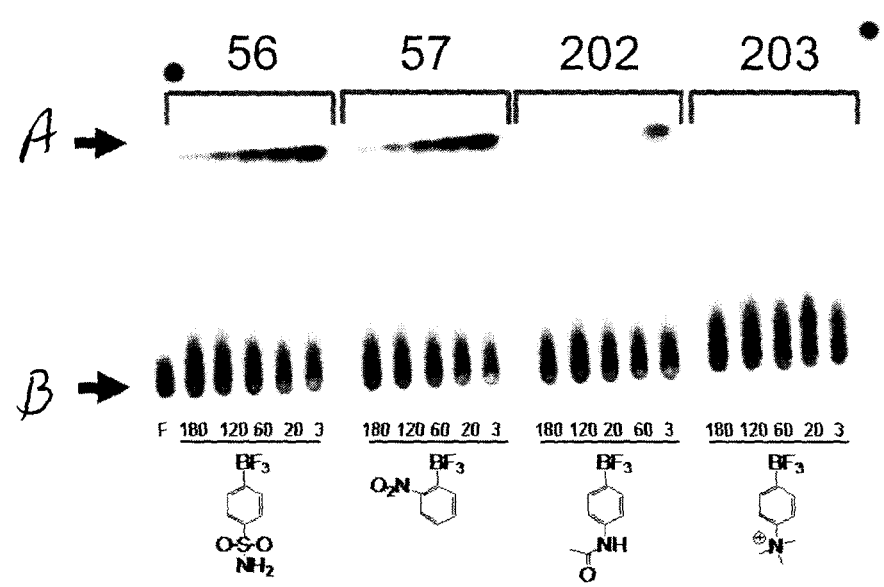
Figure 4:
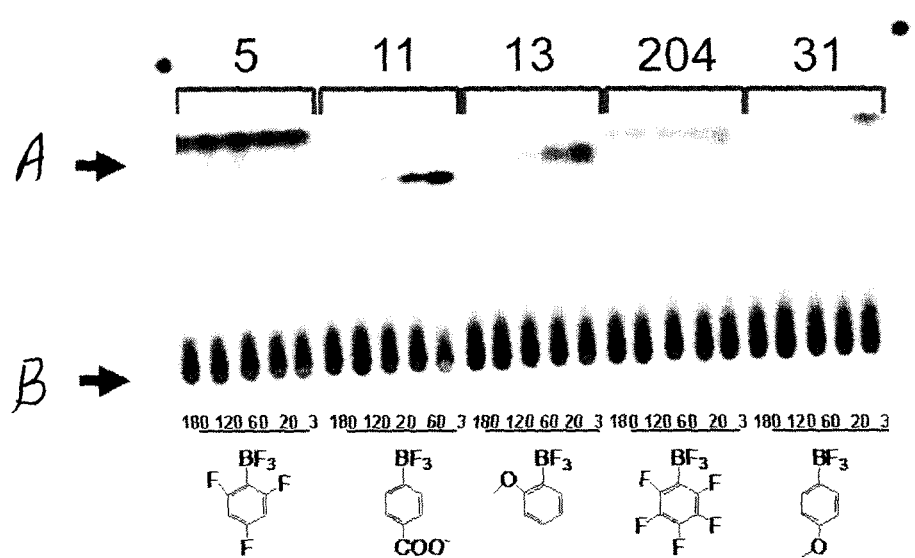

Any terms not directly defined herein shall be understood to have the meanings commonly associated with them as understood within the art of the invention. Certain terms are discussed below, or elsewhere in the specification, to provide additional guidance to the practitioner in describing the devices, methods and the like of embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention herein.

Throughout this application the terms ortho, meta, and para are defined with reference to the position of the boron containing substituent on the aryl ring. Furthermore, throughout this application aryl structures are depicted in a particular selected resonance form (e.g. see Formula 2 above). However, it will be recognised that this selection is arbitrary and does not necessarily represent the most stable canonical form of the compound.

In one embodiment, the invention relates to substituted aryl-borane or aryl-fluoroborate compounds according to the formulas described above. The substituted aryl-borate compounds also include base-free forms, prodrugs, or pharmaceutically acceptable salts thereof.

Where Y is a suitable leaving group that can be displaced by reaction with a fluoride source, m may be 2 and n may be either 0 or 1 in Formula 2. Y may be —OR$^2$, SR$^2$, NHR$^2$ or NR$^2$R$^2$ where R$^2$ is H or a substituted or unsubstituted alkyl or aryl group. In various embodiments, the leaving group atoms will be the same i.e. two oxygen atoms either with identical groups or different groups, or an oxygen atom and a nitrogen atom or a sulfur atom and a nitrogen atom as in the case of complexation with an amino acid such as serine or cysteine respectively. In various embodiments where n=0, two —OR$^2$ groups are linked together to form a five membered ring as follows:

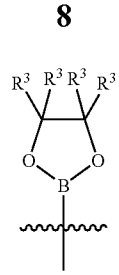

R$^3$ may be independently H, alkyl groups or aryl groups. In various embodiments R$^3$ are all methyl groups or phenyl groups. Compounds where R$^3$ are phenyl groups have enhanced stability and shelf life.

Other examples of leaving groups that can be displaced by fluoride are known. Particular examples are described in WO 2005/077967.

In Formula 2, where Y is fluorine, m may be 3 and n may be either 0, 1, or 2. In various embodiments, n is 0. F atoms may be $^{18}$F or $^{19}$F isotopes. It is recognized that stable aryltrifluoroborates (no $^{18}$F incorporated) are be useful as radiochemically stable precursors that will find use in labeling whereby they are treated under acidic conditions to promote the exchange of an atom of $^{19}$F for an atom of $^{18}$F. Following labeling, at least one of F is $^{18}$F. It is recognized that in the preparation of compounds of this invention, that there may be a fraction of molecules that will not be complexed with any $^{18}$F when carrier $^{19}$F is used. It is recognized that the addition of carrier $^{19}$F may be advantageous in certain cases. A final/overall specific activity suitable for imaging purposes can be achieved even if a particular trifluoroborate molecule in a mixture contains no $^{18}$F, provided that at least some of the trifluoroborates prepared contain at least one $^{18}$F.

The X$^{1-5}$ substituents on the ring (X$^1$, X$^2$, X$^3$, X$^4$, X$^5$) may each independently be H or any group, wherein at least one of the X substituents is an electron-withdrawing group (EWG). In various embodiments, more than one of the X substituents are EWGs. Such EWGs will be readily recognized by those skilled in the art and have been described by Hansch et al. *J. Med. Chem.* 1973, 16: 1207-1215 and have sigma values typical of electron-withdrawing groups.

A sigma value is a value that describes the electron-withdrawing properties of a particular substituent on an aromatic ring. The sigma value of a particular substituent is dependent upon the atoms which make up the substituent, the organisation of the atoms within the substituent and the position of the substituent on the aromatic ring. The sigma, or "σ", value at a particular position for a particular substituent is, in part, dependent on the position of that substituent on the aromatic ring and this is denoted by a letter in subscript following the "σ". For example "σ$_m$" and "σ$_p$" represent the sigma values of a substituent in the meta and para positions, respectively. The sigma value of substituents in the ortho position are treated herein as being the same as when the substituent is in the para position. In other words, "σ$_o$" is taken to equal that of "σ$_p$". "σ$_{total}$" represents the sum of the sigma values of all of the substituents on the aromatic ring. Representative σ$_m$ and σ$_p$ values as reported by Hansch et al. are listed in Table 1 which shows both electron-withdrawing and electron-donating substituent groups.

EWGs are those atoms or groups at a particular position (ortho/para or meta) having a sigma value that is >0 at that position, as discussed by Hansch et al. *J. Med. Chem.* 1973, 16: 1207-1215. For particular embodiments of this invention, EWGs will have σ$_m$ and/or σ$_p$ values that are >0.1. Electron-donating group are those which exhibit negative sigma values when the substituent is at the designated position (ortho/para or meta). The substituents listed in Table 1 which are electron-withdrawing at a particular position should not be considered limiting with respect to the potential scope of this invention. Those skilled in the art will readily recognize additional candidate EWG groups for particular positions and it would not require undue experimentation to determine $\sigma_m$ or $\sigma_p$ values for substituents not described in Table 1.

It is also recognized that Table 1, while by no means extensive, does not inform on issues of toxicity or metabolic stability—both of which would be considered by the skilled reader. It is also recognized that Table 1 does not inform about stability under buffered aqueous conditions. Despite favorable EWG properties, it is recognized that certain EWGs will not be stable under aqueous conditions. For instance, those trained in the art would readily recognize that substitutions such as —NCS, —NCO, —PCl$_2$, —SF$_3$, —POCl$_2$, SO$_2$F, SiCl$_3$, and —N$_2$$^+$ are readily hydrolyzed in water. Others such as PH$_2$ will readily air-oxidize. Others, such as NH$_3$$^+$ are pH dependent and at higher pH values i.e. 7, they lose their EWG properties and become electron donating. Thus, whereas sigma values would guide contemplation generating hydrolytically stable $^{18}$F-labeled trifluoroborates, other properties concerning the reactivity and/or toxicity of the substituent may contraindicate use.

TABLE 1

| Compound | sigma m | sigma p |
|---|---|---|
| B(OH)$_2$ | −0.01 | 0.12 |
| Br | 0.39 | 0.23 |
| CBr$_3$ | 0.28 | 0.29 |
| CCl$_3$ | 0.32 | 0.33 |
| CF$_3$ | 0.43 | 0.54 |
| CN | 0.56 | 0.66 |
| COO$^-$ | −0.1 | 0 |
| CHO | 0.35 | 0.42 |
| COOH | 0.37 | 0.45 |
| CH$_2$Br | 0.12 | 0.14 |
| CH$_2$Cl | 0.11 | 0.12 |
| CH$_2$I | 0.1 | 0.11 |
| CONH$_2$ | 0.28 | 0.36 |
| CH=NOH | 0.22 | 0.1 |
| CH$_3$ | −0.07 | −0.17 |
| CH$_2$OH | 0 | 0 |
| 3,4-(CF$_2$OCF$_2$) | 0.81 | 0.81 |
| C≡CH | 0.21 | 0.23 |
| CH$_2$SCF$_3$ | 0.12 | 0.15 |
| CH$_2$SO$_2$CF$_3$ | 0.29 | 0.31 |
| CH$_2$CN | 0.16 | 0.01 |
| CH=CHNO$_2$(trans) | 0.32 | 0.26 |
| CH=CH$_2$ | 0.05 | −0.02 |
| COCH$_3$ | 0.38 | 0.5 |
| CO$_2$CH$_3$ | 0.37 | 0.45 |
| CH$_2$COOH | | −0.07 |
| C=O(NHCH$_3$) | 0.35 | 0.36 |
| CH$_2$CONH$_2$ | | 0.07 |
| C=S(NHCH$_3$) | 0.3 | 0.34 |
| C$_2$H$_5$ | −0.07 | −0.15 |
| 1-(1,2-B$_{10}$H$_{10}$C$_2$H)-α-carboranyl | 0.48 | 0.52 |
| 3-Barenyl | 0.2 | 0.19 |
| 1-Neobarenyl | 0.25 | 0.33 |
| C≡CCF$_3$ | 0.41 | 0.51 |
| C(OH)(CF$_3$)$_2$ | 0.29 | 0.3 |
| CH=CHCF$_3$(trans) | 0.24 | 0.27 |
| CH=CHCF$_3$(cis) | 0.16 | 0.17 |
| CH=CHCN | 0.24 | 0.17 |
| C≡CCH$_3$ | | 0.09 |
| CH=CHCHO | 0.24 | 0.13 |
| CH=CHCOOH | 0.14 | 0.9 |
| cyclopropyl | −0.07 | −0.21 |
| CO$_2$C$_2$H$_5$ | 0.37 | 0.45 |
| CH$_2$OC=O(CH$_3$) | | 0.05 |
| CH$_2$CH$_2$COOH | −0.03 | −0.07 |
| 3,4-(CH$_2$—CH$_2$—CH$_2$) | −0.26 | −0.26 |
| C$_3$H$_7$ | −0.07 | −0.13 |
| CH(CH$_3$)$_2$ | −0.07 | −0.15 |
| CH$_2$N(CH$_3$)$_2$ | | 0.01 |
| CF$_2$CF$_2$CF$_2$CF$_3$ | 0.47 | 0.52 |
| 2-Thienyl | 0.09 | 0.05 |
| 3,4-(CH=CHCH=CH) | 0.04 | 0.04 |
| CH=CHCOCH$_3$ | 0.21 | −0.01 |
| cyclobutyl | | −0.15 |
| 3,4-(CH$_2$)$_4$ | −0.48 | −0.48 |
| C$_4$H$_9$ | −0.08 | −0.16 |
| C(CH$_3$)$_3$ | −0.1 | −0.2 |
| CH$_2$Si(CH$_3$)$_3$ | −0.16 | −0.21 |
| CH=CHCO$_2$C$_2$H$_5$ | 0.19 | 0.03 |
| cyclopentyl | | −0.02 |
| C$_5$H$_{11}$ | −0.08 | −0.015 |
| (CH$_2$)$_3$N(CH$_3$)$_2$ | | −0.13 |
| C$_6$Cl$_5$ | 0.25 | 0.24 |
| C$_6$F$_5$ | 0.34 | 0.41 |
| C$_6$H$_2$[2,4,6-(NO$_2$)$_3$] | 0.26 | 0.3 |
| C$_6$H$_5$ | 0.06 | −0.01 |
| (bicyclic structure) | | 0.15 |
| cyclohexyl | | −0.22 |
| (CH$_2$)$_3$N(CH$_3$)$_3$$^+$ | | 0.02 |
| (benzoxazolyl) | 0.3 | 0.33 |
| (benzothiazolyl) | 0.27 | 0.29 |
| C=O(C$_6$H$_5$) | 0.34 | 0.43 |
| CH=NC$_6$H$_5$ | 0.35 | 0.42 |
| CH$_2$C$_6$H$_5$ | −0.08 | −0.09 |
| CH(OH)C$_6$H$_5$ | | −0.03 |
| (bicyclic structure) | | 0.01 |
| C≡CC$_6$H$_5$ | 0.14 | 0.16 |
| CH=CHC$_6$H$_5$ | 0.03 | −0.07 |
| CH$_2$CH$_2$C$_6$H$_5$ | | −0.12 |
| CH=CHCOC$_6$H$_4$—(4-NO$_2$) | 0.15 | 0.05 |
| CH=CHCOC$_6$H$_5$ | 0.18 | 0.05 |
| Ferrocenyl | −0.15 | −0.18 |
| Adamantyl | −0.12 | −0.13 |
| (N-ethylbenzimidazolyl) | 0.17 | 0.21 |
| CO$_2$CH(C$_6$H$_5$)$_2$ | 0.36 | 0.56 |
| Cl | 0.37 | 0.23 |
| F | 0.34 | 0.06 |
| GeBr$_3$ | 0.66 | 0.73 |
| GeCl$_3$ | 0.71 | 0.79 |
| GeF$_3$ | 0.85 | 0.97 |
| H | 0 | 0 |

TABLE 1-continued

| Compound | sigma m | sigma p |
|---|---|---|
| $HgCH_3$ | 0.43 | 0.1 |
| I | 0.35 | 0.18 |
| $IO_2$ | 0.68 | 0.78 |
| NO | | 0.12 |
| $NO_2$ | 0.71 | 0.78 |
| $N{\equiv}N^+$ | 1.76 | 1.91 |
| NNN | 0.27 | 0.15 |
| $NH_2$ | −0.16 | −0.66 |
| NHOH | −0.04 | −0.34 |
| $NH_3^+$ | 0.86 | 0.6 |
| $NHNH_2$ | −0.02 | −0.55 |
| 5-Cl-1-tetrazolyl | 0.6 | 0.61 |
| $N{=}CCl_2$ | 0.21 | 0.13 |
| $N{=}C{=}O$ | 0.27 | 0.19 |
| $N{=}C{=}S$ | 0.48 | 0.38 |
| 5-azido-1-tetrazolyl | 0.54 | 0.54 |
| NHCN | 0.21 | 0.06 |
| 1-Tetrazolyl | 0.52 | 0.5 |
| 5-OH-1-tetrazolyl | 0.39 | 0.33 |
| 5-SH-1-tetrazolyl | 0.45 | 0.45 |
| NHCHO | 0.19 | 0 |
| $NHCONH_2$ | −0.03 | −0.24 |
| $NHCSNH_2$ | 0.22 | 0.16 |
| $NHCH_3$ | −0.3 | −0.84 |
| $NHSO_2CH_3$ | 0.2 | 0.03 |
| $N(CH_3)_2$ | 0.4 | 0.53 |
| $NHCOCF_3$ | 0.3 | 0.12 |
| $NHCOCH_2Cl$ | 0.17 | −0.03 |
| $NHCOCH_3$ | 0.21 | 0 |
| $NHCSCH_4$ | 0.24 | 0.12 |
| $NHC_2H_5$ | −0.24 | −0.61 |
| $N(CH_3)_2$ | −0.15 | −0.83 |
| $NHCO_2Et$ | 0.07 | −0.15 |
| NHCONHEt | 0.04 | −0.26 |
| NHCSNHEt | 0.3 | 0.07 |
| $NMe_3^+$ | 0.88 | 0.82 |
| $NHCOCHMe_2$ | 0.11 | −0.1 |
| $NHCH_2CO_2Et$ | −0.1 | |
| NH—nBu | −0.34 | −0.51 |
| $N{=}NC_6H_5$ | 0.32 | 0.39 |
| $NHC_6H_5$ | −0.12 | −0.4 |
| $NHSO_2C_6H_5$ | 0.16 | 0.01 |
| $N{=}CHC_6H_5$ | −0.08 | −0.55 |
| $N(C_6H_5)_2$ | 0 | −0.22 |
| $NHCOC_6H_5$ | 0.02 | −0.19 |
| $N{=}NC_6H_3(2\text{-}OH)(5\text{-}CH_3)$ | 0.27 | 0.31 |
| $N{=}CHC_6H_4{-}(4\text{-}OCH_3)$ | −0.07 | −0.54 |
| $NHCOC_6H_4{-}(4\text{-}OCH_3)$ | 0.09 | −0.06 |
| $O^-$ | −0.47 | −0.81 |
| OH | 0.12 | −0.37 |
| $3,4\text{-}(OCF_2O)$ | 0.36 | 0.37 |
| $OCF_3$ | 0.38 | 0.35 |
| $OCHF_2$ | 0.31 | 0.18 |
| $3,4\text{-}(OCH_2O)$ | −0.16 | −0.16 |
| $OCH_3$ | 0.12 | −0.27 |
| $OSO_2CH_3$ | 0.39 | 0.36 |
| $OCF_2CHFCl$ | 0.35 | 0.28 |
| $OCOCH_3$ | 0.39 | 0.31 |
| $OCH_2COOH$ | | −0.33 |
| OEt | 0.1 | −0.24 |
| $OPO(OCH_3)_2$ | | 0.04 |
| $OCH(CH_3)_2$ | 0.1 | −0.45 |
| $OC_3H_7$ | 0.1 | −0.25 |
| $OC_4H_9$ | 0.1 | −0.32 |
| $OC_5H_{11}$ | 0.1 | −0.34 |
| $OC_6H_5$ | 0.25 | −0.03 |
| $OSO_2C_6H_5$ | 0.36 | 0.33 |
| $OCOC_6H_5$ | 0.21 | 0.13 |
| $POCl_2$ | 0.8 | 0.43 |
| $PCl_2$ | 0.53 | 0.61 |
| $POF_2$ | 0.81 | 0.89 |
| $PF_2$ | 0.26 | 0.61 |
| $PSCl_2$ | 0.73 | 0.39 |
| $PO_3H^-$ | 0.2 | 0.26 |
| $PH_2$ | 0.05 | |
| $P(Cl)NN(Me)_2$ | 0.38 | 0.56 |
| $PO(Me)_2$ | 0.42 | |
| $PO(OMe)_2$ | 0.42 | 0.53 |
| $PMe_3$ | 0.03 | 0.31 |
| $P(OEt)_2$ | | 0.33 |
| $PO(OEt)_2$ | 0.55 | 0.6 |
| $PO(Cl)C_6H_4{-}3\text{-}F$ | 0.65 | |
| $P(Cl)C_6H_4{-}3\text{-}F$ | 0.42 | |
| $PS(Cl)C_6H_4{-}3\text{-}F$ | 0.56 | |
| $P(Cl)C_6H_5$ | | 0.44 |
| $PS(CH_3)C_6H_4{-}3\text{-}F$ | 0.09 | |
| $PO(OPr)_2$ | 0.38 | 0.5 |
| $P(OCH_3)C_6H_4{-}3\text{-}F$ | 0.33 | |
| $PO(CH_3)C_6H_4{-}3\text{-}F$ | 0.4 | |
| $P(CH_3)C_6H_4{-}3\text{-}F$ | 0.2 | |
| $PO(Bu)_2$ | 0.35 | 0.49 |
| $PO(C_6H_5)_2$ | 0.38 | 0.53 |
| $P(C_6H_5)_2$ | 0.11 | 0.19 |
| $PS(C_6H_5)_3$ | 0.29 | 0.47 |
| $SO_2(F)$ | 0.8 | 0.91 |
| $SF_3$ | 0.61 | 0.68 |
| $SO_2^-$ | −0.02 | −0.05 |
| $SO_4^-$ | 0.05 | 0.09 |
| SH | 0.25 | 0.15 |
| $SO_2(NH_2)$ | 0.46 | 0.57 |
| $S{=}O(CF_3)$ | 0.63 | 0.69 |
| $SO_2(CF_3)$ | 0.79 | 0.93 |
| $SCF_3$ | 0.4 | 0.5 |
| SCN | 0.41 | 0.52 |
| $SCHF_2$ | 0.33 | 0.37 |
| $SOCHF_2$ | 0.54 | 0.58 |
| $SO_2CHF_2$ | 0.75 | 0.86 |
| $SOCH_3$ | 0.52 | 0.49 |
| $SO_2CH_3$ | 0.6 | 0.72 |
| $SCH_3$ | 0.15 | 0 |
| $SCF_2CHF_2$ | 0.38 | 0.47 |
| $SCOCH_3$ | 0.39 | 0.44 |
| $SC_2H_5$ | 0.18 | 0.03 |
| $S(CH_3)_2$ | 1 | 0.9 |
| $SO_2(C_6H_5)$ | 0.61 | 0.7 |
| $SC_6H_5$ | | 0.18 |
| $S(CH_3){=}NSO_2{-}(C_6H_4{-}4\text{-}CH_3)$ | 0.65 | 0.7 |
| $SeCF_3$ | 0.32 | 0.39 |
| SeCN | 0.61 | 0.66 |
| $SeCH_3$ | 0.1 | 0 |
| $SiBr_3$ | 0.48 | 0.57 |
| $SiCl_3$ | 0.48 | 0.565 |
| $SiF_3$ | 0.54 | 0.69 |
| $SiMe_3$ | −0.04 | −0.07 |
| $Si(CH_3)_2[OSiMe_3]$ | 0 | −0.01 |
| $Si(CH_3)[OSiMe_3]_2$ | −0.02 | −0.01 |
| $Si[OSiMe_3]_3$ | −0.09 | −0.01 |
| bis(tetrazolyl disulfide) structure | 0.63 | 0.64 |
| thiadiazoline structure [dp1] | 0.30 | 0.19 |

Differences between the $\sigma_m$ and $\sigma_p$ value for a particular substituent reflect the fact that the overall electron-withdrawing/donating character of the substituent is determined by both inductive (I) and mesomeric (M) effects. Thus, describing a group as an EWG relates to its relative location in the molecule in question with respect to the other functional or substituent groups and the boron atom.

Definitions and descriptions of how the inductive and mesomeric effects interact are known in the art, and further details may be found in, for example "*Advanced Organic Chemistry—Reactions, Mechanisms and Structure*", 3$^{rd}$ ed.

by J. March 1985 Wiley Interscience. Groups are classified relative to H. For example an $NO_2$ group draws electrons to itself more than an H atom would if it occupied the same position in the molecule in question. Examples of inductive (–I) EWG groups include $NR_3^+$, —COOH, —OR, —COR, —SH, —SR, —OH, aryl, halogens such as —F, —Cl, —Br, or —I; α-haloalkyl groups, —O-aryl, —COOR, —$SR_2^+$, —$NH_3^+$, —$NO_2$, —$SO_2R$, —$SO_2$aryl, —CN. Other examples of –I groups are described in Hansch, supra, and include those having $\sigma_m$ values that are greater than zero.

The electron-withdrawing mesomeric, or resonance, effect arises from the comparison of a compound with a closely related donor, or a real compound with a canonical form. An electron-withdrawing group of this type (–M) may include an atom or a group of atoms having a multiple-bonded electronegative atom directly connected to an unsaturated system. An $NO_2$ group is one exemplary –M group. Other examples of –M groups include —CN, —COOH, —COOR, —$CONH_2$, —CONHR, —$CONR_2$, —CHO, —COR, —$SO_2R$, —$OCF_3$ (trifluoromethoxy), —$OCHF_2$ (difluoromethoxy) and —$OCOCH_3$ (i.e. O-acetyl) —$OCOC_6H_5$ (O-benzoyl), and —$OSO_2R$(O-sulfonyl). Other examples will be known to those skilled in the art, and may be found in, for example Hansch, supra.

Mesomeric effects are position dependent, with only those substituents placed in ortho and para positions on the ring contributing a mesomeric effect. Furthermore, substituents can be both –I (i.e. electron-withdrawing by inductive effects) and +M (i.e. electron donating by mesomeric effects). This explains why a group that is traditionally considered an EWG may have a much higher value for $\sigma_m$ than for $\sigma_p$.

For the ortho positions ($X^1$ and $X^5$ substituents) steric effects are also important. These effects can overcome the negative effect on fluoride retention of a group with electron donating character found as a substituent in these positions. Due to this influence of sterics on reactivity for ortho-substituents, $\sigma_p$ values, i.e. a measure of the electron-withdrawing capacity in the ortho positions, is often not readily accessible. However, since the mesomeric (resonance) effects of a group in the ortho and para positions are equivalent, one may use the $\sigma_p$ value as a surrogate for the purely electronic component of $\sigma_p$.

EWG's have particular properties that may be better suited to one position on the ring over another and EWG's suited for the ortho ($X^1$ and $X^5$), meta ($X^2$ and $X^4$), and para ($X^3$) positions on the aryl ring differ in scope with respect to each other. For example, steric bulk along with electron-withdrawing character is more desirable at the ortho positions, than in either the meta or para positions. EWG's that may be suited for situation at the meta position ($X^2$ and $X^4$) often have $\sigma_m$ values >0. In some embodiments, substituents in the meta position have $\sigma_m$ values >0.1. The para position may have a reduced tolerance for any +M character and substituents that may be suited for situation at the para position ($X^3$) may have $\sigma_p$ values >0. In various embodiments the para position substituent may have a $\sigma_p$ value of >0.06. Steric effects may provide for higher tolerances of weakly electron-withdrawing or even electron donating groups in the $X^1$ and/or $X^5$ positions.

By way of example, Table 2 describes the effect on the half-life (minutes) of defluorination for various monosubstituted aryl-trifluoroborate compounds of the following general structural formula.

TABLE 2

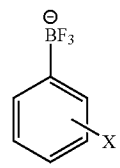

| X | Position of X on ring | | |
|---|---|---|---|
| | p | m | o |
| —$OCH_3$ | $t_{1/2}$ = 3 minutes | | 20 |
| —$SCH_3$ | 4 | | 48 |
| —F | 4 | | 58 |
| —$CF_3$ | 18 | | 190 |
| —CN | 57 | 38 | 180 |

Referring to Table 2, and recognizing that $\sigma_p$ values are used as a surrogate for $\sigma_o$, the electronic effect can be readily seen moving from an electron donor substituent (—OMe, $\sigma_p$=–0.27), through to an effectively electroneutral substituent (—SMe, $\sigma_p$=0), a weak electron-withdrawing group (—F, $\sigma_p$=0.06), and finally to strongly electron-withdrawing groups (—$CF_3$, $\sigma_p$=0.54; —CN, $\sigma_p$=0.66, $\sigma_m$=0.56). In accordance with the invention, the electron-withdrawing character of the substituent increases so does the half live of defluorination.

There are also differences between the half-lives of defluorination for para-substituted compounds as compared to ortho-substituted compounds, showing that steric effects will also affect the rate of defluorination. This steric effect is further substantiated by a comparison of the m,m (left panel) and o,o (right panel) analogs of the following disubstituted bis(trifluoromethyl) analogs.

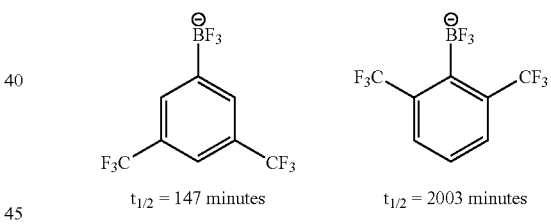

$t_{1/2}$ = 147 minutes    $t_{1/2}$ = 2003 minutes

While both compounds fall within the scope of this invention, with $\sigma_p$ (0.54) and $\sigma_m$ (0.43) values for a $CF_3$ group, further increase in stability comes from the steric effect of having two relatively bulky $CF_3$ groups situated beside the trifluoroborate moiety in the o,o analog.

Table 3 depicts the effect of exemplary groups that are capable of anchimerically assisting (i.e. neighboring group participation) defluorination (minutes) of trifluoroborate groups in the ortho-position.

TABLE 3

| X | Position of X on ring | | |
|---|---|---|---|
| | p | m | o |
| —CHO | $t_{1/2}$ = 34 minutes | 21 | 41 |
| —$NO_2$ | 30 | 37 | 35 |

Both —CHO ($\sigma_p$=0.42, $\sigma_m$=0.35) and —$NO_2$ ($\sigma_p$=0.78, $\sigma_m$=0.71) are strongly electron-withdrawing groups and as such, when substituted onto the para or meta positions of the ring show half-lives of defluorination of a similar magnitude to their —CF₃ and —CN analogs. However, when substituted in the ortho-position the half-lives are lower than those displayed by the CF₃ and CN substituted compounds. This is due to the ability of substituents such as —CHO, —NO₂, and COOH to assist defluorination through mechanisms such as:

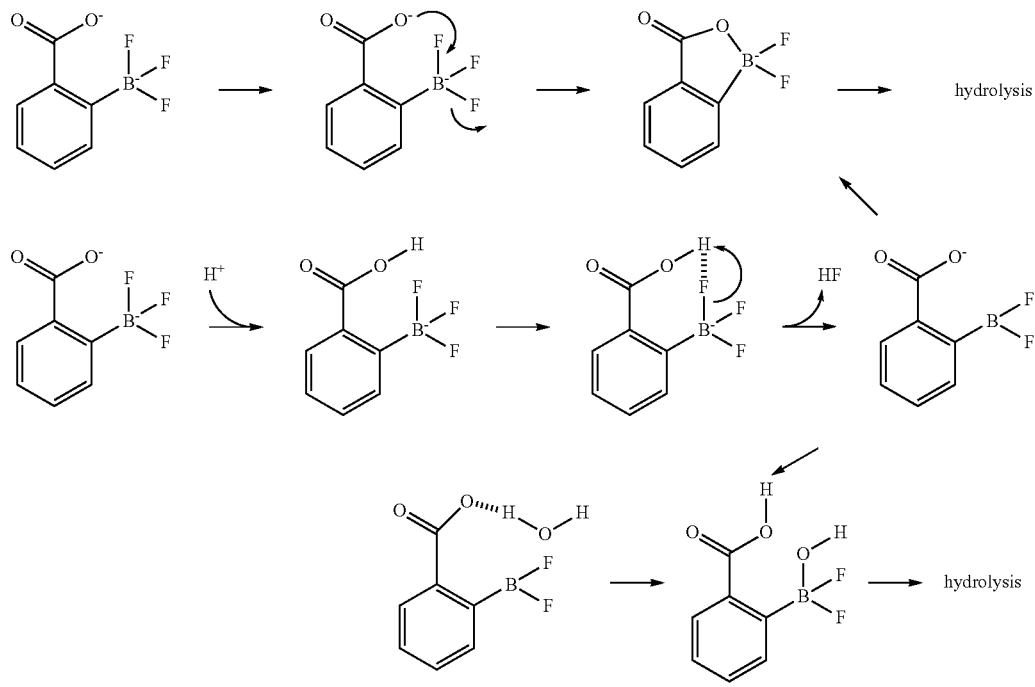

A further example of a trifluoroborate compound affected by anchimeric assistance is the following, which has a half-life of about 4 minutes despite containing two relatively strongly electron-withdrawing groups (CH₃OCO, $\sigma_p$=0.45; F, $\sigma_m$=0.34).

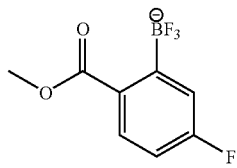

Various methods are known in the art to assess the influence of a substituent group in an aromatic system on the exchange or solvolysis of an indicator group. An example of such a system includes the cumyl chloride assays as described by Okamoto and Brown, *J. Am. Chem. Soc.* 1958 80: 4976-9 and Okamoto, Inukai and Brown *J. Am. Chem. Soc.* 1958 80: 4969-72. In these assays, a group on the phenyl ring of cumyl chloride that enhances the conversion of cumyl chloride to cumene ($E_1$ elimination), or solvolysis to cumyl alcohol or corresponding ethers (e.g. methylethers) ($SN_1$ substitution) may be considered electron donating. Conversely, a group that slowed or prevented such conversion or solvolysis may be considered an EWG. In some embodiments of the invention, an EWG includes an EWG according to such a cumyl chloride assay.

An additional criterion for addressing the desired placement of substituents on a phenyl ring relative to boron, relate to electrophilic aromatic substitution reaction profiles, for example, nitration or bromination. Groups considered to be activating ortho-para directors substituted on a phenyl ring at positions $X^1$, $X^3$ and/or $X^5$ will reduce the half-life, unless these groups afford steric encumbrance in which case they may be contemplated at the ortho positions 2. Alternatively, groups that are deactivating ortho-para directors (for example, halogens) at these positions do not reduce half-life as is the case with groups considered to be meta directing.

While bulky groups may not be desired in particular cases, sterics can be used to offset the otherwise undesirable effects of an electron donating group. For instance, an isopropoxy group would be better than a methoxy group at a particular site.

In particular embodiments, EWG's that are suitable for situation at $X^2$ and $X^4$ are those groups that have individual $\sigma_m$ values of greater than 0.1 and still other embodiments have individual $\sigma_m$ values of >0.15 or >0.2 and in other embodiments, substituents with higher values will be chosen. Example groups include α-haloalkyl groups such as —CF₃, —CCl₃, —CF₂R, CCl₂R; or other groups such as F, Br, Cl, OR, —CN, —SO₂R—, —NO₂, —CN, SR, C(O)R, C(O)OR, C(O)NHR, and SO₂NHR. R may be an optionally substituted aryl group or an optionally substituted, linear or branched or cyclic, saturated or unsaturated, one to fifteen carbon alkyl group.

In particular embodiments, EWG's that are suitable for situation at $X^3$ are those groups that have a $\sigma_p$ value of greater than 0.1 and still other embodiments have a $\sigma_p$ value of >0.15 or >0.2. Example groups include α-haloalkyl groups such as —CF₃, —CCl₃, CL₃, —CF₂R, CCl₂R, —CBr₂R, CL₂R (where L is any halogen); or other groups such as Br, Cl, —CN, —SO₂R—, —NO₂, —CN, —COOH, —COOR, —CONH₂, —CONHR, —CONR₂, —CHO, —COR, —CO₂OR, SO₂NHR, SO₂OR, SO₂NR₂. R may be an optionally substituted aryl group or an optionally substituted, linear or branched or cyclic, saturated or unsaturated, one to fifteen carbon alkyl group.

In particular embodiments, EWG's that are suitable for situation at $X^1$ and $X^5$ are those groups that have a $\sigma_p$ value of greater than 0. Some embodiments have a $\sigma_p$ value of greater than 0.1 and still other embodiments have a $\sigma_p$ value of >0.15 or >0.2. However it can be desirable that groups that are capable of anchimerically assisting defluorination of the fluoroborate moiety are not be found in the $X^1$ or $X^5$ positions. Exemplary groups that may be less desirable at either $X^1$ or $X^5$ include —SO$_2$R, —NO$_2$, —COOH, —COOR, —CONH$_2$, —CONHR, —CONR$_2$, —CHO, —C(O)R, —CO$_2$OR (when R is alkyl or aryl). More generally such less desirable groups can be defined according to the following general formula: -Q(=E)$_a$(Y)$_b$, where Q is C, N, P or S; E is O, S or NR; Y is R, OR, OOR, NR$_2$, H or O$^-$; a is 1 and, where Q is S or P may also be 2; and b is 1 or 2 (when R is alkyl or aryl).

Groups that are more desirable at $X^1$ and $X^5$ include, for example, α-haloalkyl groups such as —CF$_3$, —CCl$_3$, —CF$_2$R, CCl$_2$R; or other groups such as OR, SR, F, Br, Cl, I, and —CN. R may be H or an optionally substituted aryl group or an optionally substituted, linear or branched or cyclic, saturated or unsaturated, one to fifteen carbon alkyl group. In particular embodiments one or both of $X^1$ and $X^5$ are independently F, Cl, Br, CF$_3$, I, or CN.

In various embodiments, two or more of $X^1, X^2, X^3, X^4, X^5$ are electron-withdrawing groups that have been appropriately selected according to their $\sigma_m$ or $\sigma_p$ character.

It is possible to assess the total electron-withdrawing power of the substituent groups on the aryl ring by simply summing the sigma values using $\sigma_p$ as a surrogate for $\sigma_o$, i.e. $\sigma_{total} = \sigma_p^{X1} + \sigma_m^{X2} + \sigma_p^{X3} + \sigma_m^{X4} + \sigma_p^{X5}$. In other words, the sum of each of the sigma values for all of the substituents on the aromatic ring, where the sigma value of the substituents in the ortho position are the same as the sigma value of the same substituents as if they were in a para position, provides a total electron-withdrawing value for the aromatic ring with all of the substituents in terms of a sigma value. In particular embodiments, compounds for use in this invention have at least one ortho substituent and a $\sigma_{total}$ of about 0.5 or more. Other embodiments provide compounds that do not comprise an ortho substituent with a $\sigma_{total}$ of more than about 1.0 or more.

At least one of the substituents $X^1, X^2, X^3, X^4$, and $X^5$ may be capable of conjugating to a suitable biomolecule through suitable linker chemistry such as that described in WO 2005/077967.

Linking groups may include aliphatic or aromatic moieties designed to insulate the biomolecule from the boron atom by an appropriate distance or to ensure that appropriate atoms are adjacent the boron atom to facilitate the fluorination process. Groups which facilitate subsequent addition of a biomolecule are well known in the art and may include moieties which readily form a bond to a selected biomolecule, a variety of such groups being known in the art. These include thiol and amine reactive groups and other such groups which may be useful for joining a compound of this invention to functionalities on biomolecules including hydroxide, carboxylic acid, amine, sulfhydryl groups, etc. It is recognized that certain linker groups are less desirable for situation in the ortho ($X^1$ and $X^5$) positions due to potential to anchimerically or protolytically assist defluorination but may be situated in the $X^2$, $X^3$, or $X^4$ positions. Further contemplated herein is the joining of a compound of this invention to a biomolecule through bonds other than covalent bonds. Thus, groups, which provide for ionic, hydrophobic and other non-covalent to a biomolecule are contemplated. Exemplary linker groups for facilitating coordination to a biomolecule include:

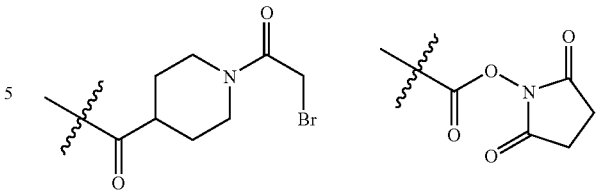

The term 'biomolecule' as used herein refers to a biomolecule, or analog or derivative of a biomolecule, or other molecule that may be delivered into a human or animal in order to track or image distribution of the biomolecule within a human or animal body or tissue via positron emission tomography. Examples are disclosed in WO 2005/077967.

In some embodiments, a "biomolecule" refers to any molecule of medical, physiological or scientific significance, analog or derivative thereof that is compatible with a biological system or which possess biological activity. Biomolecules may be delivered into a human or animal and include biomolecules that become localized at particular places in the organism. Examples include sugars, amino acids, nucleic acids, nucleotides, nucleosides, peptide hormones (steroid and non-steroid), antibodies, aptamers and oligonucleotides, proteins, peptides, oligonucleotides, lipids, hormones, drugs (synthetic drugs and natural products), polysaccharides, liposomes, micelles, microsomes, magnetic particles, metal chelators, oligoribonucleotides, oligonucleotides and related analogs bearing modifications in the backbone, nucleobase, or phosphate linker regions that enhance stability or modulate specificity, peptidomimetics, dendrimers, drug delivery agents, nanotubes, fullerenes, virus particles, and other targeting molecules (e.g. cancer targeting molecules). Specific examples include, but not limited to, biotin, matrix mettaloprotease inhibitors such as marimastat, insulin, somatostatin, somatotropin, somatomedin, adrenocorticotropic hormone, parathormone, follicle stimulating hormone, luteinizing hormone, epidermal growth factor, thyroid stimulating hormone, thyroid stimulating hormone releasing hormone, luteinizing hormone releasing hormone, vasopressin, bombesin, endothelin, gonadotropins, gonadotropin releasing hormone, antiflamin I&II, NLE-antiflamin II, brain natriureitic peptide, calcitonin, corticotropin releasing peptide, oxytocin, calpain inhibitor peptide, alpha-CGRP, corticotropin releasing factor, galanin, growth hormone releasing factor, guanylin, alpha-helical corticotropin releasing factor, laminin, alpha-melanocyte stimulating hormone, platelet derived growth factor, neuromedin, neurotensin, pancreatic polypeptide, pentagastrin, peptide-YY, pituitary adenylate cyclase activating peptide, secretin, thyrotropin releasing hormone, urocortin, vasoactive intestinal peptide, vasopressin, vascular endothelial growth factor, apamin, bungarotoxin, calciceptin, charybdotoxin, cobrotoxin, conotoxin, dendrotoxin, melittin, neuropeptide-Y, imperatoxin, taycatoxin, annexin, inhibin, insulin-like growth factor, prolactin, melanin stimulating hormone, melanin concentrating hormone, substance-P, tachykinin, angiotensin, antibodies of general structural classes of IgG, IgM, IgE, IgA, as well as single-chain, monoclonal, and recombinant forms used for current and anticipated imaging, diagnostic, and therapeutic applications. Specific targets that can be recognized by antibodies comprise without limitation: melanoma cell, melanoma specific antigen, myelin basic protein, breast cancer specific tumor markers such as Her2-Neu and Brc-Abl, alpha-fetoprotein, human chorionic gonadotropin, prostate specific antigen, prostate specific membrane antigen, epidermal growth factor receptors, fibroblast growth factor receptor, insulin receptor. Other examples are antibodies approved for use in therapy such as Herceptin™ (Amgen), Erbitux™ (Imclone). Polymers containing nucleobases and nucleotides including RNA, DNA, and PNAs and various synthetic derivatives thereof that reflect modification of the sugar, internucleoside linkage (backbone) and nucleobase portions are also contemplated. Oligonucleotides that can be used for imaging, for example: antisense oligonucleotides that target mRNA of genes implicated in the disease state, siRNA or RNAi molecules that target mRNA via RNA silencing, and aptamer structures which represent a diverse class of folded nucleic acid structures that target protein or glycoforms of proteins or both, or folded RNA structures. Further examples are aptamers approved for clinical use or those intended for clinical and diagnostic use such as Macugen™ (Eyetech) and aptamers that are used in the context of surface arrayed aptamers for diagnostic purposes, oligosaccharides of both synthetic and natural origin that are found on the surface of cellular receptors or can mimic the glycoforms of cellular receptors and proteins. Other saccharide components in synthetic glycoforms are sialic acid, mannose, fucose, N-acetyl-glucosamine, N-acetyl-mannosamine, maltose, galactose and N-acetyl-galactosamine, small to mid-size molecular weight ligands for proteins comprise various classes of compounds, for example: porphyrins, lectins, lipids, steroids, barbiturates, taxanes, terpenes, terpenoids, canabinoids, opioids, nucleosides, purines, pyrimidines, heteroaromatics, quinolines, biogenic amines, amino acids, indole-alkaloids, topane alkaloids, statins, enzyme inhibitors, nonsteroidal anti-inflammatory agents, monosaccharides, folates, derivatives of folate, methotrexate, derivatives of methotrexate, trexates, vitamins, growth hormone, VEGF, EGF, an antibody, a breast cancer antigen specific antibody, a prostate cancer antigen specific antibody, a melanoma antigen specific antibody, a ligand, a RGD-motif ligand recognizing a matrix metalloprotease, an aptamer, an aptamer recognizing a cell surface protein, folic acid, a folic acid derivative and a methotrexate.

Particular arylborane and arylfluoroborate compounds for use in this invention are defined in the above described Formulas and as well, by the following:

Other possible heterocyclic core structures comprise the following:

Particular arylborane (m=2) and arylfluoroborate (m=3) compounds to be fluorinated for use in this invention are described in Table 4. The compounds may be further substituted with an appropriate linker group, for conjugation to a biomolecule, as described above at any of the aryl-H sites. Potential positions at which linker groups to biomolecules may be are indicated with an arrow (→). Bold dots show examples of sites for biomolecule attachment.

TABLE 4

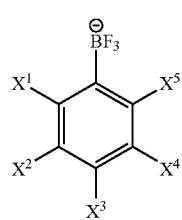

TABLE 4-continued
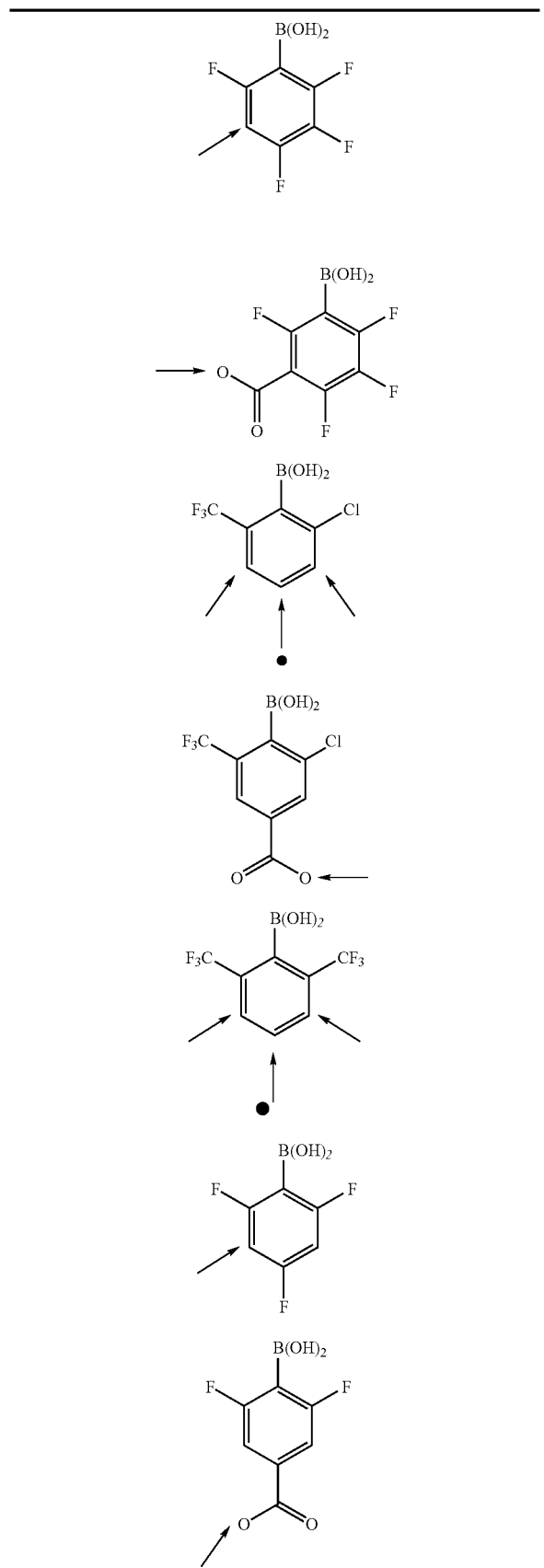
TABLE 4-continued
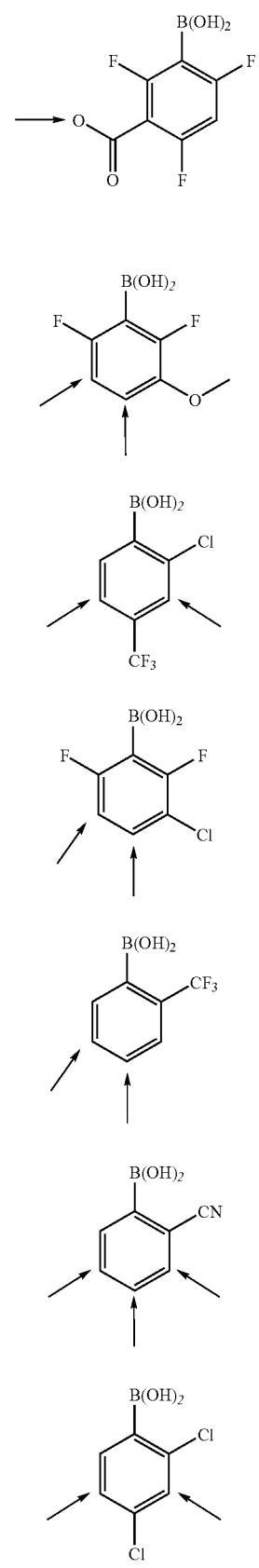

TABLE 4-continued

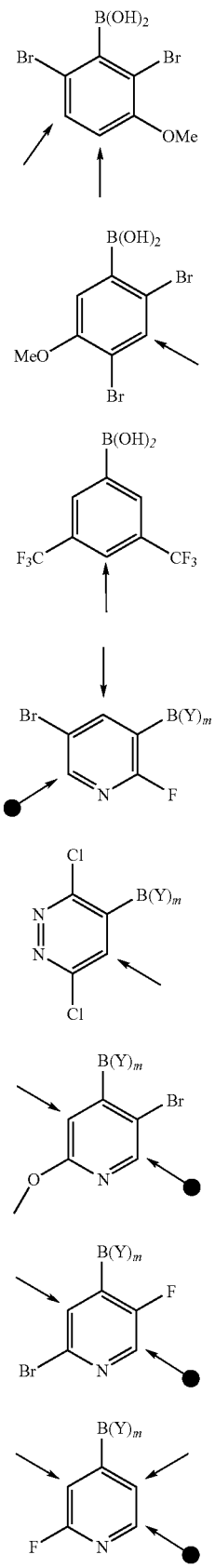

TABLE 4-continued

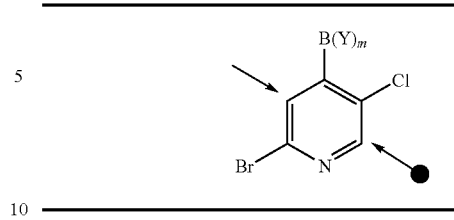

Table 5 shows arylborate compounds and the experimentally obtained half-life of defluorination of their trifluoroborate products.

TABLE 5

| Compound # | Structure | Half-life (min) |
|---|---|---|
| 2 | (dansyl sulfonamide-phenyl boronic acid) | 19 ± 1 |
| 4 | 2,6-difluoro-4-methoxyphenylboronic acid | 94 ± 10 |
| 5 | 2,4,6-trifluorophenylboronic acid | 234 ± 37 |
| 8 | 4-cyanophenylboronic acid | 57 ± 4 |
| 9 | 2-cyanophenylboronic acid | 180 ± 46 |
| 10 | 2,4-dichlorophenylboronic acid | 313 ± 66 |

TABLE 5-continued

| Compound # | Structure | Half-life (min) |
|---|---|---|
| 11 | 4-carboxyphenylboronic acid | 13 ± 1 |
| 12 | 3-carboxyphenylboronic acid | 10 ± 1 |
| 13 | 2-methoxyphenylboronic acid | 20 ± 1 |
| 14 | 2-fluorophenylboronic acid | 58 ± 6 |
| 15 | 2-chlorophenylboronic acid | 98 ± 9 |
| 16 | 2-(trifluoromethyl)phenylboronic acid | 190 ± 22 |
| 17 | 3-formylphenylboronic acid | 21 ± 2 |
| 18 | 4-(trifluoromethyl)phenylboronic acid | 26 ± 3 |
| 19 | 4-formylphenylboronic acid | 34 ± 3 |
| 20 | 2-formylphenylboronic acid | 41 ± 4 |
| 21 | 2-(methylthio)phenylboronic acid | 48 ± 4 |
| 22 | 2,3-difluorophenylboronic acid | 126 ± 22 |
| 23 | 3-cyanophenylboronic acid | 38 ± 2 |
| 24 | 2,4-dimethoxyphenylboronic acid | 4 ± 1 |
| 25 | 4-iodophenylboronic acid | 18 ± 5 |
| 26 | 4-acetylphenylboronic acid | 22 ± 2 |

TABLE 5-continued

| Compound # | Structure | Half-life (min) |
|---|---|---|
| 28 | 3,4-difluorophenylboronic acid | 13 ± 2 |
| 29 | 2,4-difluorophenylboronic acid | 52 ± 5 |
| 30 | 4-(methylthio)phenylboronic acid | 3 ± 0.3 |
| 31 | 4-methoxyphenylboronic acid | 3 ± 1 |
| 32 | 4-fluorophenylboronic acid | 4 ± 0.2 |
| 33 | 4-chlorophenylboronic acid | 5 ± 0.2 |
| 34 | 3-nitrophenylboronic acid | 37 ± 1 |
| 50 | 4-(methylthio)phenylboronic acid pinacol ester | 4 ± 0.3 |
| 53 | 2-chloro-4-(trifluoromethyl)phenylboronic acid | 571 ± 31 |
| 54 | 4-(methylsulfonyl)phenylboronic acid pinacol ester | 52 ± 6 |
| 55 | 2-(methylthio)phenylboronic acid pinacol ester | 50 ± 5 |
| 56 | 4-sulfamoylphenylboronic acid pinacol ester | 41 ± 4 |
| 57 | 2-nitrophenylboronic acid | 35 ± 2 |
| 58 | 2,3,4,6-tetrafluorophenylboronic acid pinacol ester | 1181 ± 298 |
| 59 | 2,6-bis(trifluoromethyl)phenylboronic acid | 2003 ± 763 |

TABLE 5-continued

| Compound # | Structure | Half-life (min) |
|---|---|---|
| 72 | 2-chloro-4-(trifluoromethyl)phenylboronic acid | 288 ± 48 |
| 84 | 3-chloro-2,6-difluorophenylboronic acid | 507 ± 97 |
| 86 | 2,5-difluoro-4-methoxyphenylboronic acid | 60 ± 5 |
| 87 | 2,6-difluoro-3-methoxyphenylboronic acid | 345 ± 204 |
| 90 | 3,5-bis(trifluoromethyl)phenylboronic acid | 147 ± 34 |
| 95 | 2,6-difluoropyridin-4-ylboronic acid | 242 ± 44 |
| 102 | 4-fluoro-3-methoxyphenylboronic acid | 13 ± 5 |
| 103 | 4-bromo-3-methoxyphenylboronic acid | 463 ± 68 |
| 104 | 2,5-dibromo-4-methoxyphenylboronic acid | 454 ± 86 |
| 106 | 5-(methylsulfonyl)pyridin-3-ylboronic acid | 275 ± 29 |
| 111 | 2,6-dibromo-3-methoxyphenylboronic acid | 576 ± 306 |
| 112 | 4-bromo-2-chloro-5-methoxyphenylboronic acid | 391 ± 58 |
| 117 | 4-fluoro-2-(methoxycarbonyl)phenylboronic acid | 4 ± 0 |
| 118 | 4-carbamoyl-3-chlorophenylboronic acid | 40 ± 2 |
| 122 | 3-aminophenylboronic acid | 3 ± 0.1 |
| 128 | 4-carboxy-3-methoxyphenylboronic acid | 24 ± 7 |

TABLE 5-continued

| Compound # | Structure | Half-life (min) |
|---|---|---|
| 151 | (3-ethoxy-2-fluorophenyl)boronic acid | 143 ± 23 |
| 152 | (2-fluoro-5-methoxyphenyl)boronic acid | 143 ± 8 |
| CH-01-059 | 4-carboxy-2,6-difluorophenyl pinacol boronate | 410 ± 144 |
| RT 9-089 | 3-carboxy-2,4,6-trifluorophenyl pinacol boronate | 781 ± 95 |
| 200 | (4-nitrophenyl)boronic acid | 47 ± 4 |
| 201 | (4-dimethylaminophenyl)boronic acid | <3 min |
| 202 | (4-acetamidophenyl)boronic acid | <4 min |
| 203 | (4-trimethylammoniophenyl)boronic acid | 31 min |
| 204 | pentafluorophenylboronic acid | >300 min |

Arylborate compounds may be chemically elaborated as per the arylfluoroborate (m=3) examples shown in Table 6 where X is a site for joining to a biomolecule and R is —OH or —OR$^1$.

TABLE 6

[Structures showing arylboronate compounds with B(Y)$_m$ groups and X linker sites]

TABLE 6-continued
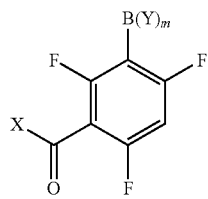
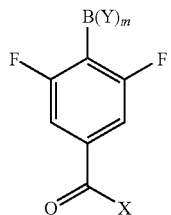
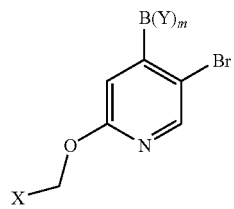
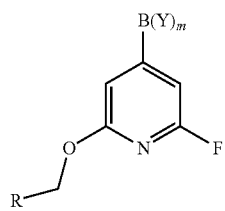
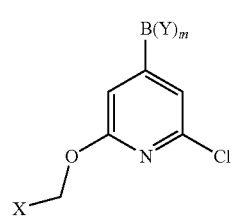
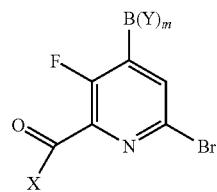
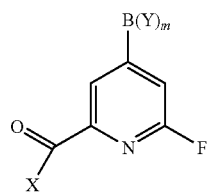
TABLE 6-continued
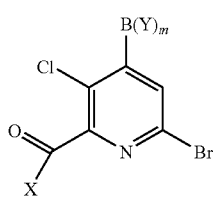
Examples of precursor compounds are shown below;
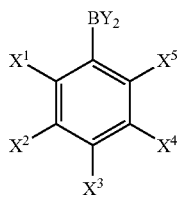
Formula 7
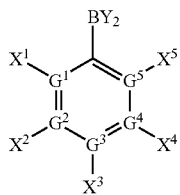
Formula 8
In particular embodiments of Formulas 7 and 8, Y is —$OR^2$ or —$SR^2$, and $R^2$ is H or a substituted or unsubstituted alkyl or aryl group. Both Y may also be joined as in the following precursor.
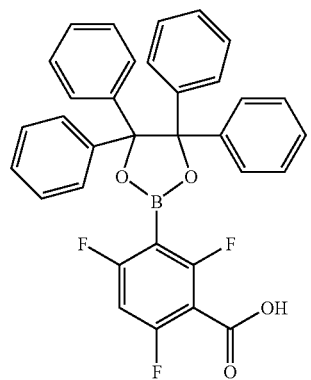 [SMILES: O=C(O)c1c(F)cc(F)c(B2OC(c3ccccc3)(c3ccccc3)C(c3ccccc3)(c3ccccc3)O2)c1F]

These compounds may be converted to activated molecules for linking to biomolecules. The following are examples of such procedures:

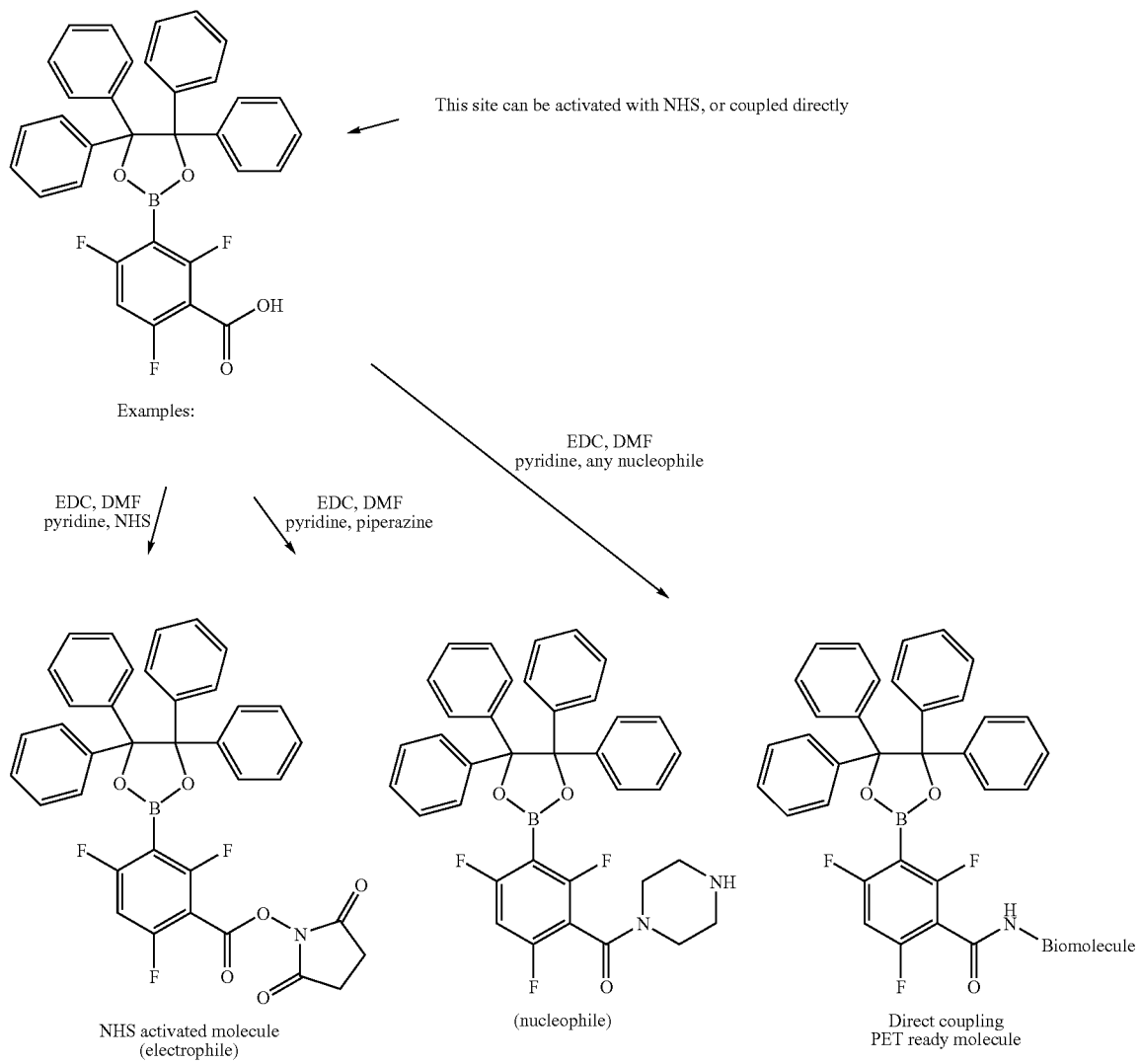

EDC is 1-Ethyl-3-[3-dimethylaminopropyl]carbodiimide hydrochloride and DMF is dimethylformamide.

In another embodiment, the invention involves methods of synthesis of substituted aryl-borate compounds, their salts or prodrugs. Substitutions on a heterocycle comprising boron will influence its aqueous stability. Stability may be kinetic and or thermodynamic. If there is no change in the overall thermodynamics of the reaction, then any retarding effect of a substitutent on the rate of solvolytic defluorination likely also retards the rate of fluorination. And by the same corollary, any group that enhances the rate of defluorination will result in an enhanced rate of fluorination. Thus, electron donating groups favor efficient or high yielding fluorination reactions, but can also enable a more rapid rate of exchange and loss of fluoride to an aqueous solvent in the form of free fluoride, accompanied by solvolytic reversion to the substituted aryl-boronic acid. Although an electron-withdrawing group may reduce the rate of fluorination and thus the overall yield at any given time-point, the electron-withdrawing group nevertheless represents a favored substituent group based on the kinetic stability it affords with respect to defluorination. Although the rate of fluorination may also be retarded, lower trifluoroborate yields are not a problem so long as the resulting specific activity remains sufficient for applications. Also, the trifluoroborate products may be separated from their starting materials such as by chromatography. The desired properties of EWG substituents with regards to retarding the solvolytic defluorination can more than offset decreases in yields of the labeling reaction. However, increased yields may be favoured through use of increased concentrations of fluoride or the boronic acid (or both), elevated temperatures, reduced pressure, and/or microfluidic reactors for the labeling reaction that increase the concentration of the reaction components.

Suitable reaction times for the preparation of trifluoroborates may be in the range of minutes, to tens of minutes and up to one hour. Longer reaction times may be contemplated if the resulting composition has correspondingly enhanced aqueous stability.

Tracer molecules used in this invention may be conjugated to a ligand such as a biomolecule that preferentially interacts with a tissue type or cell type of interest. In some embodiments of the invention, a precursor substituted aryl-boronic acid may be pre-conjugated to a biomolecule of interest and subsequently fluorinated when needed in a one-step aqueous fluorination reaction. A typical reaction may occur in a buffered solution of $KHF_2$ where the $^{18}F$ is generated in carrier free form and supplemented with carrier $^{19}F$ either at the time of fluorination or during a chase reaction.

Substituted aryl-borate compounds according to a formula described herein may be made by a variety of synthetic methods, ranging in complexity from de novo synthesis to a 'wash-in' of the fluorine on a previously prepared borate. Complete synthesis of a substituted aryl-borane or the fluorinated, substituted aryl-borate may be done according to a variety of known methods, for example those described in U.S. Pat. No. 7,087,755.

A 'wash-in' preparative method may include preparation of a solution of a substituted aryl-boronic acid or ester in an appropriate solvent, to which aqueous fluoride is added. The pH may be at a suitable range (e.g. about 4 to about 5) or according to what is suitable for the solvents and the substituted aryl-boronic acid or ester. The solvent may be DMF or another solvent that is miscible with an aqueous fluoride solution, and solubilizes the substituted aryl-boronic acid or ester of interest. Examples of such solvents may include aqueous mixtures comprising DMSO, DMF, MeOH, THF, MeCN, DMA, and NMP. Selection of a particular solvent may vary with the particular substituted aryl-boronic acid or ester and in particular with regards to preserving the bioactivity of the biomolecule, and is within the skill of one versed in the art. Aqueous fluoride may be at any suitable concentration. For example, the substituted aryl-boronic acid may be present at a concentration of about 1-4 mM, and the $KH^{18/19}F_2$ may be present in 3 or 4 equivalents i.e. 3-12 mM or 4-16 mM, where the minimal concentrations are selected to increase the specific activity of the labeling, and the maximal concentrations determined by the maximal solubility of the bioconjugate.

Clinical preparations of a substituted aryl-boronic acid or ester may involve use of about 800 mCi $^{18}F$ in carrier free form, which, barring environmental contamination with $^{19}F$, represents about 0.46 nmol of $^{18}F$, or 3.8% of the total fluoride used in a 10 µL reaction at 12 mM total fluoride. Microreactor and microfluidic techniques, (which provide reaction volumes of about 50 nL) can reduce the quantity of carrier $^{19}F$ needed. For instance in a 50 nL reaction at 10 mM fluoride, one needs only 500 pmol of total fluoride. Thus, a no carrier added reaction is readily contemplated for labeling arylboronic acids.

Reaction temperature may be increased above room temperature, but below a temperature that may destabilize or denature the selected biomolecule. For example, some nucleic acids or oligonucleotides may be suitable for use in labeling reactions at temperatures of about 60° C., while some proteins may require lower temperatures. Antibodies are known in the art to have limited thermostability compared to most other proteins however thermostable antibodies and enzymes may also be suitable for use in labeling reactions at temperatures above room temperature. Alternatively, some biomolecules may be preferentially suitable for labeling reactions at reduced temperatures, i.e. below room temperature.

General approaches and methods for direct chemical modification of biomolecules for addition and/or substitution of modifying groups are known. As an example, chemical modification of proteins is described by Means and Feeney *Bioconjugate Chemistry* 1990 1: 2-12). Chemical modification of nucleic acids such as DNA and RNA is described in, for example, Boutourine et al. *Bioconjugate Chemistry* 1990 1:350-56. Chemical modification of sugars and oligosaccharides is described in, for example Wood et al. *Bioconjugate Chemistry* 1992 3: 391-6.

Examples of compounds linked to biotin are shown below.

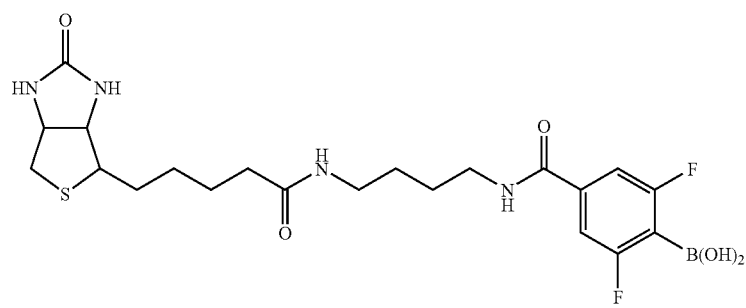

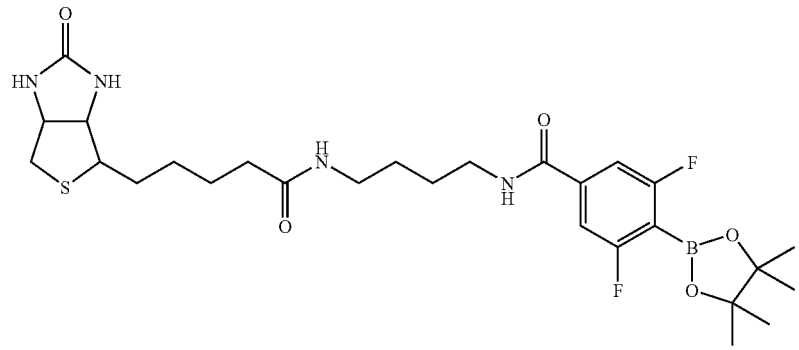

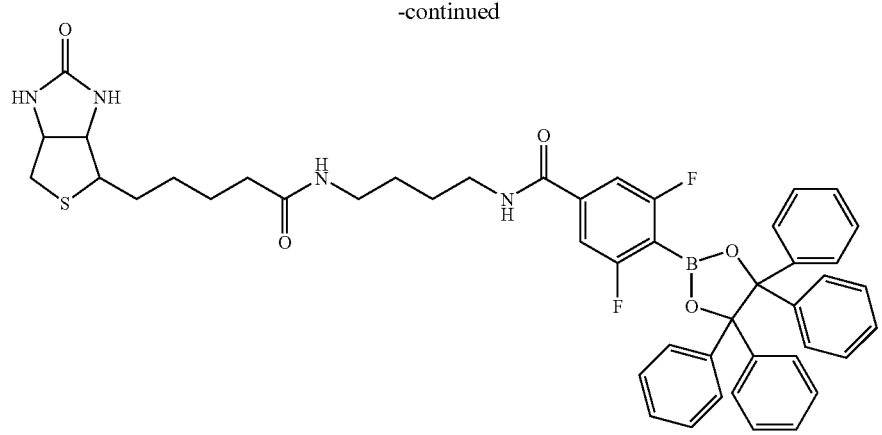
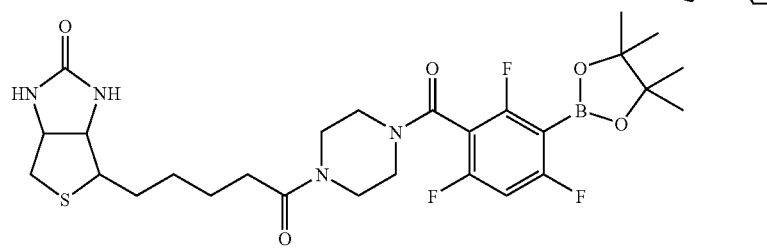
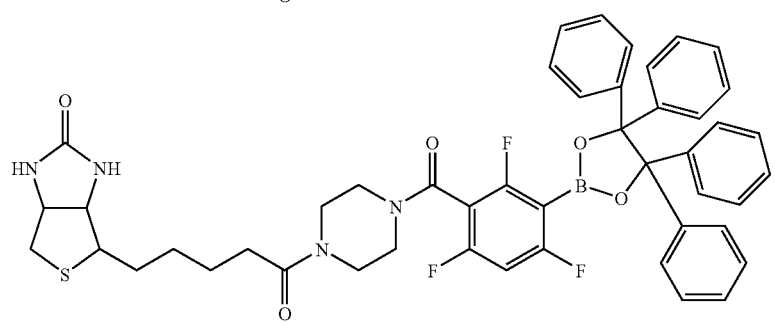
Another class of bioconjugates exemplified here that are useful for cancer and/or inflammation imaging are conjugates of marimastat. Marimastat is a hydroxamate with high specificity for MMP's. Shown below are conjugates of two phenylboronic acids/esters to marimastat.
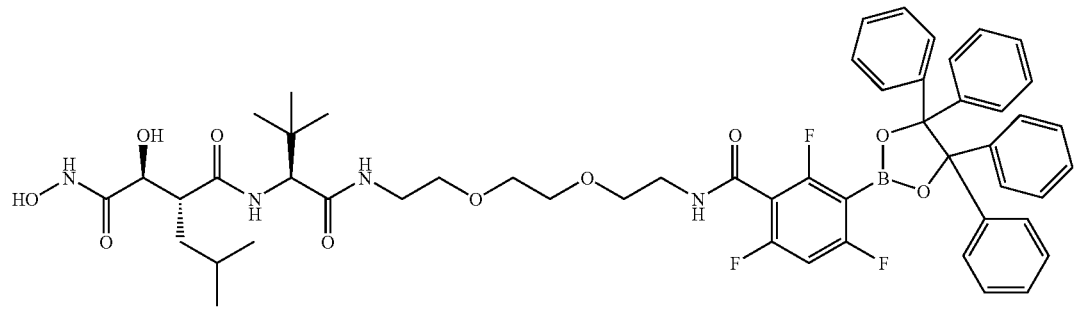
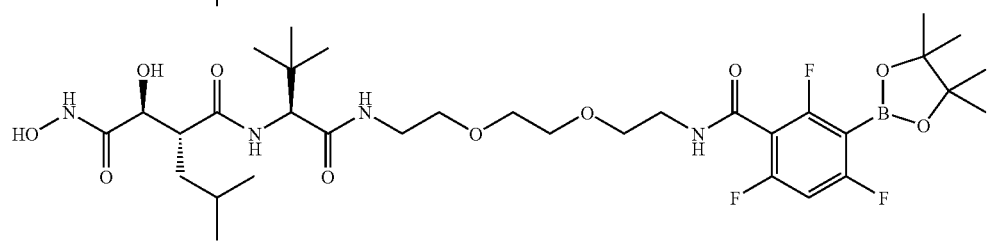

-continued

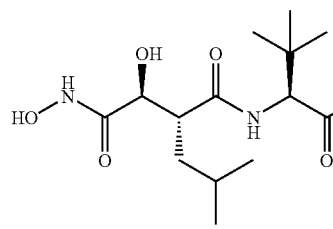
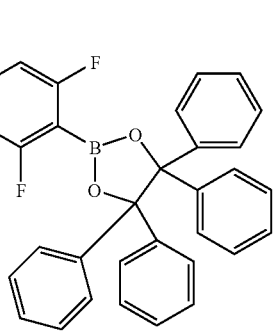
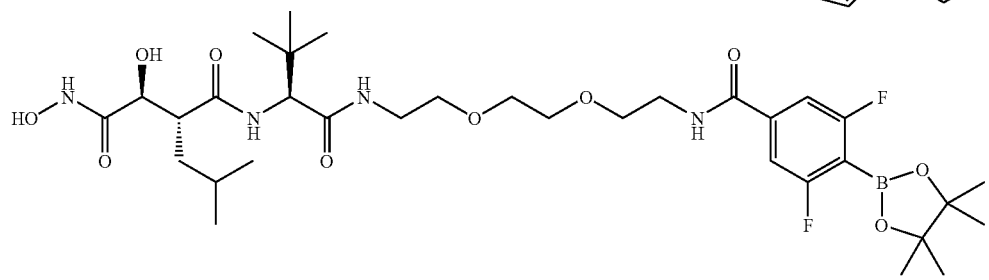

Chromatographic methods for separation of a fluorinated compound from the free $^{18}F$ are useful for qualitative or semi-quantitative assessment of the resistance to defluorination of the fluorinated compound. Such methods generally involve a stationary phase, which may be a column matrix having qualities such as hydrophobicity, porosity or size-exclusion capabilities, charge, hydrophilicity or the like. Alternately, the stationary phase may provide structural support only, and be largely inert to interactions with a mobile phase or the solutes in the mobile phase. The stationary phase may be further supported in, for example, a column, or for thin-layer chromatography, on a glass plate. Paper used in paper chromatography may provide both the stationary phase and physical support of the stationary phase.

The mobile phase is frequently a solvent, which may be hydrophobic or hydrophilic, aqueous or non-aqueous, and may be formulated to provide a fixed pH or a selected pH range, or a particular salt or other solute concentration. In various embodiments, the molecules or compounds of interest, such as the fluorinated compounds above are soluble in the mobile phase, as is the free fluorine that is to be separated from the fluorinated compound.

Choice of a particular chromatographic method may be influenced by the molecule to be separated. For example, separation of a labeled biomolecule, such as an antibody, gel-permeation or affinity chromatography may be suitable. In another example, separation of a labeled oligonucleotide or peptide, anion exchange chromatography may be suitable. In another example, separation of labeled biotin complexed with an avidin-conjugate may involve gel-permeation chromatography. In another example, separation of labeled free biotin, folate or methotrexate or other small molecules, such as peptides may involve chromatographic separation through a silica column or plug, or HPLC/FPLC.

General principles, methods and background relating to chromatography are known, and may be found in, for example, Jonsson, J. A. *Chromatographic Theory and Basic Principles*. 1987. Marcel Dekker, or Ahuja S. *Chromatography and Separation Science*. 2003. Elsevier Press; Cox, G. B. *Preparative Enantioselective Chromatography*. 2005. Blackwell Publishing; Wall, P. E. *Thin-layer chromatography: a modern practical approach* 205. Royal Society of Chemistry; Sherma, J. and Fried, B. *Handbook of Thin-layer chromatography*. 2003. Marcel Dekker.

$^{19}F$-NMR may be also used to monitor defluorination (e.g. see Ting et. al. (2008) J. Org. Chem. 73:4662-70; Harwig et. al. (2008) Tetrahedron Letters 49:3152-56; and, Ting et. al. (2008) Journal of Fluorine Chemistry 129:349-58).

Isotopic wash-out or pulse-chase methods may also be used for screening labeled trifluoroborates in order to identify compositions that are suitably stable for use as imaging agents.

EXAMPLES

Example 1

Evaluation of Rates of Defluorination

The following is a representative example of synthesis and testing of a fluorinated arylborate as shown in FIGS. 1-4. A solution of boronic acid/ester at approximately 200 mM in 3 μl DMF is made, and 3 μL of aqueous fluoride at 800 mM added, comprising ~1 mCi of carrier free $^{18}F$ (~0.6 pmol of $^{18}F$) and carrier $^{19}F$ in the form of $KHF_2$ in 800 mM HOAc at pH 3-4, in a total volume of 10 μl at 10 mM total, providing 100 nmol of total fluoride at a pH of 4.5. Following a one hour labeling reaction at room temperature, the extent of fluorination as well as the stability with regards to isotopic exchange is evaluated by thin layer chromotography TLC as described below.

1 μL of the fluorination mix is diluted 1:100 in 200 mM phosphate buffer pH 7.5, 100 mM $K^{19}F$ and allowed to equilibrate. A "zero" time point is taken, consisting of 1 μL of the fluorination mix added to the above phosphate-KF solution, mixed and then 0.5 μL of this dilution is immediately spotted on a TLC plate. An equal amount (0.5 μL) of the other samples representing longer time points from 0-180 minutes) are also spotted in a similar manner. A separate dilution is made for each time point. Spots are dried on the plate briefly in ambient air. An [18/19]F-only spot from a dummy fluorination reaction diluted as described is spotted as a control, to locate free fluoride. Free fluoride is separated from the parent molecule using a mobile phase of 5% $NH_4OH$ 95% EtOH, for a migration distance of 5-8 cm (approximately 30 minutes). Following resolution, the plate is dried in ambient air or with a blow drier at low heat and exposed to a phosphoimager screen to permit visualization of the isotope migration. Other low boiling solvents such as methanol, 1- and 2-propanol, 1- and 2-butanol, and acetonitrile can also be used instead of or in conjunction with ethanol. The amount of $NH_4OH$ may vary from as little as 0.5% to as much as 20%. Water may be added to the mobile phase and such variation will afford different $R_f$ values and separations.

Autoradiograms of TLC plates showing migration and relative amount of retained $^{18}$F are shown in FIGS. 1-4. Specific structures are shown below the time points for each experiment. Fluoride dissociation shows a time-dependence that varies with the functional groups associated with the conjugated system. For example, compounds #12 and 22 appear to retain the fluorine radioisotope longer than compounds 10 or 19, with other compounds falling in a range between these. The presence of an electron-withdrawing group (EWD) on the aryl ring promotes longer retention of the fluorine radiolabel. The presence of a group having steric bulk greater than that of H in an ortho position also promotes a longer retention of the fluorine radiolabel.

To calculate a rate constant and half-life of the $ArBF_3$, the $ArBF_3$ is prepared usually at 100 mM $ArB(OH)_2$ and 400 mM fluoride at pH 4.5 at a given specific activity of [18]F. In most cases, the fluoridation reaction is found to be complete after one hour. Once completed, an aliquot (1.5 µL) from the fluorination reaction solution is the added to a volume of 300 µL of a chase solution containing 200 mM phosphate and 100 mM KF (pH 7.5). Aliquots from the stock solution are added to the chase solution for varying lengths of times. Then 1 µL of the chase solution from each time point is spotted on a TLC plate and chromatographed. Autoradiograms are then generated and analyzed by a phosphoimager. The densities of the free fluoride spot and the $ArBF_3$ spot are quantified. To calculate a rate constant and half-life, the following calculation is performed: 1) the percentage of counts attributed to the $ArBF_3$ at t=0 is calculated (density in the $ArBF_3$ spot divided by the sum of the densities of the $ArBF_3$ spot and the free fluoride spot). This gives a t=0 value. 2) The same is performed for each of the other spots corresponding to other time points—this serves to normalize for any differences in the number of cpm loaded on the plate. 3) The value for each time point including that for t=0 is divided by the value calculated for t=0. This serves to normalize for how much $ArBF_3$ remains at any given time as a percentage. These points are then fit using Sigma plot to the function $f(x)=Ae^{-kt}$ to obtain a rate constant k reflecting the rate of fluoride exchange and the half-life is given as 0.69/k. In cases where fluorination was not complete in one hour, a number of fluorination reactions equal to the number of time points were prepared. They were then quenched and allowed to exchange their fluoride for varying times but where the quench was added in each case one hour after the fluorination was initiated.

Example 2

Application of a Novel Borate-Bioconjugate in PET Imaging

An example of an electron-withdrawing aryl-borate coupled to a biomolecule is shown below. The particular biomolecule is marimastat, a non-specific target of metallomatrix proteins commonly over expressed by certain cancers. It is converted to its trifluoroborate upon the addition of an aqueous fluoride solution. The $^{18}$F labels on the boron may instead be any combination of at least one $^{18}$F and any number of [19]Fs.

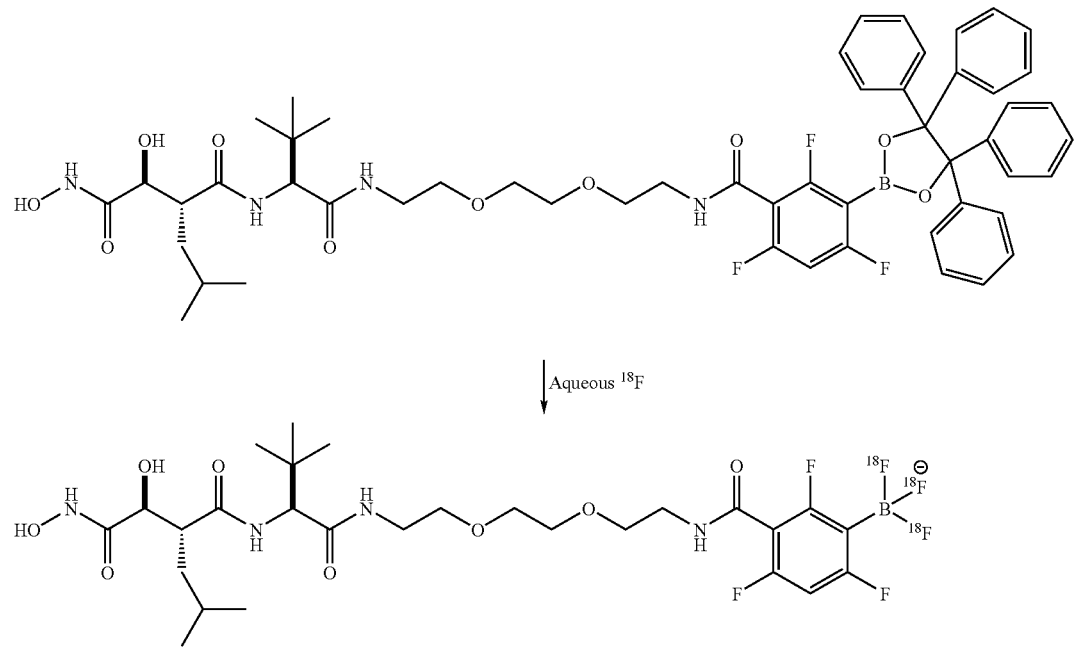

A mouse bearing a human carcinoma near its bladder was imaged with the $^{18}$F-marimastat composition buffered to and injected with phosphate buffered saline at pH 6. The $^{18}$F-marimastat solution was introduced through a tail vein injection. Positron emission tomography images were reconstructed from images obtained following a 60 minute from the time of injection. Biodistribution of "$^{18}$F-marimastat" differed from that of Fluoride-18 ($^{18}$F$^-$) which typically ends up in the bladder and skeletal system after 60 minutes. Target organs of "$^{18}$F-marimastat" included the bladder, the liver, and organs within the mouse's head with an absence of $^{18}$F in the skeletal system of the mouse. This indicates that the imaging agent retained fluoride as a trifluoroborate.

Table 7 describes an $^{18}$F biodistribution study on a carcinoma bearing mouse imaged with the $^{18}$F marimastat as described above.

TABLE 7

| Test Tube | Tissue | Total Scintillation Counts (0.5 min) | Organ Mass (g) | Counts Per Gram |
|---|---|---|---|---|
| 1 | primary tumor | 595727 | 0.28 | 2 127 596 |
| 2 | liver | 316161 | 0.19 | 1 664 005 |

TABLE 7-continued

| Test Tube | Tissue | Total Scintillation Counts (0.5 min) | Organ Mass (g) | Counts Per Gram |
|---|---|---|---|---|
| 3 | kidney | 198964 | 0.17 | 1 170 376 |
| 4 | spleen | 63171 | 0.05 | 1 263 419 |
| 5 | heart | 74699 | 0.15 | 497 993 |
| 6 | lung | 52275 | 0.06 | 871 249 |
| 7 | uterus | 111517 | 0.1 | 1 115 170 |
| 8 | background | 59 | 0 | N/A |

Example 3

In Vivo Pet Imaging with Biotin Conjugated ArB [$^{18}$F][$^{19}$F]$^-$

We examined in vivo stability of a biotinylated version of an ArBF$_3^-$ i.e. biotinyl-ArB[$^{18}$F][$^{19}$F]$_2^-$ (3) and describe its radiofluoridation from its precursor boronic ester (2) as a captor for aqueous [$^{18}$F]-fluoride as shown in below.

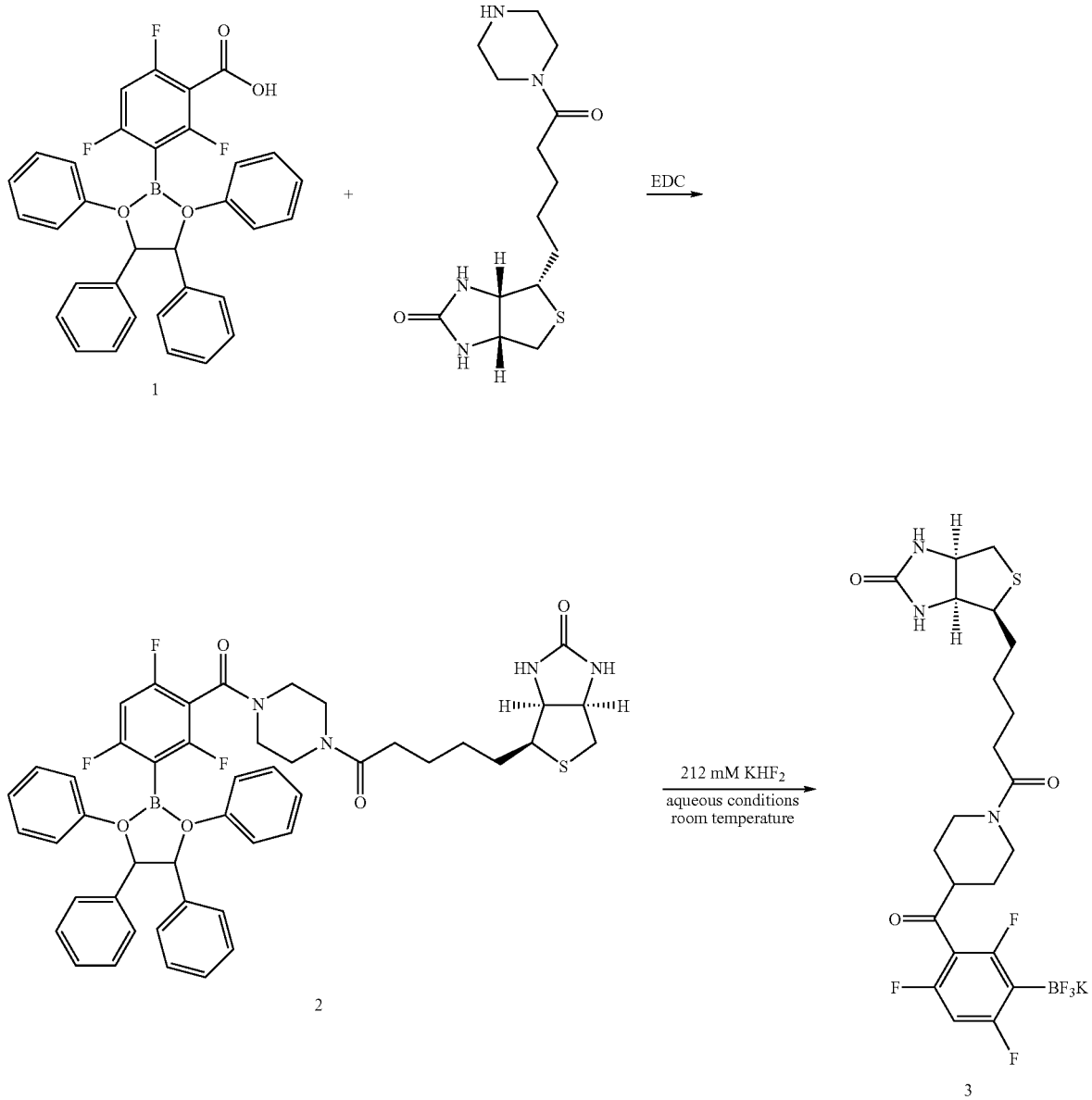

Chemicals were purchased from Sigma, Aldrich, or Acros Organic. Deuterated solvents were purchased from Cambridge Isotope Laboratories. Analytical and preparative thin layer chromatography experiments were run on Silica Gel 60 $F_{254}$ Glass TLC plates from EMD Chemicals. All $^1$H Nuclear magnetic resonance (NMR) spectra were recorded on a Bruker Avance™ 300 or 400 MHz instrument. Chemical shifts are reported using the δ scale in ppm and all coupling constants (J) are reported in hertz (Hz). Unless specified, $^1$H-NMR spectra are referenced to the tetramethylsilane peak (δ=0.00) and $^{19}$F-NMR spectra are referenced to NEAT trifluoroacetic acid (δ=0.00, −78.3 ppm relative to $CFCl_3$). Due to the presence of [$^{19}$F]-fluoride contamination in the NMR spectrometer probe, baseline corrections for samples less than 20 mM in [$^{19}$F]-fluoride concentration had to be adjusted by multipoint linear baseline correction using MestReC 4.9.9.9. This correction did not affect the absolute chemical shifts or integration ratios of $^{19}$F signals.

Piperazine Biotinamide: Biotin (0.34 g, 1.4 mmols) was dissolved in 8 mL of neat thionyl chloride. This reaction was allowed to proceed for 5 min before the reaction was placed under vacuum where excess thionyl chloride was removed. The resulting oil was resuspended in 10 mL of $CH_2Cl_2$ and dried down. This process was repeated three times in order to drive off excess thionyl chloride. A solution of piperazine (0.54 g, 6.3 mmols) dissolved in 30 mL of pyridine was added to the resulting oil. This solution was stirred overnight, concentrated and the resulting solid was triturated with 40 mL of MeOH. The MeOH soluble material was collected by filtration, concentrated, and triturated with 40 ml of $CH_2Cl_2$. The $CH_2Cl_2$ soluble material was collected by filtration, concentrated and chromatographed on a 1 cm silica column with 2:98 $NH_4OH$:ethanol as the running solvent. Elution was monitored by TLC where the product displays an $R_f$ of 0.80 with a 33:67 $NH_4OH$:EtOH developing solution. The appropriate fractions were concentrated to give 42.9 mg of the piperazine biotinamide as a white solid in a 10% yield.

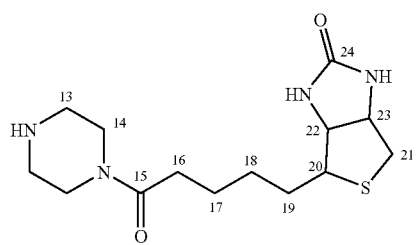 [SMILES: O=C1NC2CSC(CCCCC(=O)N3CCNCC3)C2N1]

$^1$H NMR ($CDCl_3$, 300 MHz): 4.47-4.45 (m, 1H, $CH^{23}$), 4.30-4.26 (m, 1H, $CH^{22}$), 3.55 (m, 2H, $CH_2^{14}$), 3.42 (m, 2H, $CH_2^{14'}$), 3.14-3.12 (m, 1H, $CH^{20}$), 2.92-2.80 (m, 4H, $CH^{13'}$), 2.43-2.30 (m, 4H), 1.71-1.61 (m, 4H), 1.45-1.40 (t, J=7.4 Hz, 2H). HRMS (ESI) calculated for $C_{14}H_{24}N_4NaO_2S^+$ (M+Na)$^+$: 335.15121, found: 335.1516.

(2) (2-(1,3,5-trifluoro-4-(4, 4, 5,5-tetraphenyl-1,3,2-dioxaborolan-2-yl)benzoyl) piperazin-1-yl) biotin: To a 4 mL vial containing 3.55 mL of DMF in the following order: piperazine biotinamide (23.7 mg, 0.076 mmols), pyridine (33.2 μL, 0.41 mmols), HOBt monohydrate (13.5 mg, 0.10 mmols, (1) (50 mg, 0.09 mmols), (1,3,5-Trifluoro-4-(4,4,5,5-tetraphenyl-1,3,2-dioxaborolan-2-yl)benzoic acid) prepared as described by Ting et al. *J Fluorine Chemistry* [supra], and EDC (19.4 mg, 0.10 mmols). This reaction was left for 16 hours after which it was concentrated to oil and loaded onto a 0.5 cm silica column. Compound (2) was eluted with 10:90 MeOH:$CHCl_3$. Elution was monitored by TLC where (2) displays an $R_f$ of 0.50 with a 30:70 MeOH:$CHCl_3$ developing solution. The appropriate fractions were concentrated to give 55.9 mg of (2) (a 73.3% yield) as a white solid.

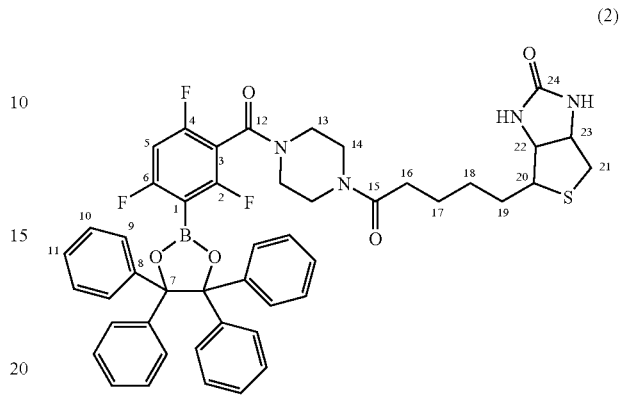

$^1$H-NMR ($CD_2Cl_2$, 400 MHz): 7.22 (m, 4H, $CH^9$), 7.21-7.20 (m, 4H, $CH^{9'}$), 7.14-7.11 (m, 12H, $CH^{10,11}$), 6.91 (t, J=8.8 Hz, 1H, $CH^5$), 4.48 (m, 1H, $CH^{23}$), 4.31 (m, 1H, $CH^{22}$), 3.84-3.81 (m, 2H), 3.71-3.39 (m, 7H), 3.17 (m, 1H), 2.93-2.84 (m, 1H), 2.72-2.69 (m, 1H), 2.44-2.34 (m, 2H), 1.75-1.68 (m, 4H), 1.29 (m, 2H). $^{19}$F NMR ($CD_2Cl_2$, 300 MHz): −17.43 (1F), −22.61 (1F), −28.93 (1F). HRMS (ESI) calculated for $C_{47}H_{44}BF_3N_4NaO_5S^+$ (M+Na)$^+$: 867.29697, found: 867.2977.

(3) (2-(1,3,5-trifluoro-4-(trifluoroboryl)benzoyl)piperazin-1-yl) biotin

A $^1$H-NMR tube containing 475 μl of MeOH was charged with (2) (8.0 mg, 9.4 μmol) and 25 μl of a 4 M $KHF_2$ solution (200 μmol fluoride). The kinetic profile of trifluoroborate formation was monitored by $^{19}$F-NMR. The extent to which the reaction proceeded was gauged by the appearance of a trifluoroborate peak (TFB) at −59 ppm. Following completion of the reaction, the entire contents of the NMR tube were eluted through a Pasteur pipet packed with 600 mg of dry Silicycle 230-400 mesh silica. (3) was eluted in the first 500 μl with 5% $NH_4OH$/EtOH as the eluant. This chromatography step facilitated the quantitative removal of free fluoride.

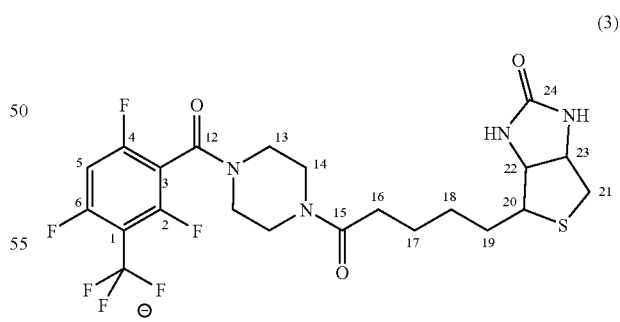

$^1$H NMR (MeOH-d4, 400 MHz): 6.66 (t, J=9.2 Hz, 1H, $CH^5$), 4.48 (m, 1H, $CH^{23}$), 4.31 (m, 1H, $CH^{22}$), 3.85-3.80 (m, 2H), 3.73-3.35 (m, 7H), 3.25-3.20 (m, 1H), 2.93-2.90 (m, 1H), 2.72-2.69 (m, 1H), 2.49-2.41 (m, 2H), 1.75-1.60 (m, 4H), 1.29 (m, 2H)$^{19}$F NMR (5% $NH_4OH$/EtOH, 300 MHz): −20.70 (s, 1F, CF), −29.20 (s, 1F, CF), −41.23 (s, 1F, CF), −59.90 (br, 3F, $BF_3$). HRMS (ESI) calculated for $C_{21}H_{24}BF_6N_4O_3S^-$ (M)$^-$: 537.15718.0 m/z. found: 537.3.

$^{18}$F preparation: The desired activity of $^{18}$F was prepared through the bombardment of 1 mL of H$_2$$^{18}$O water with 12.5 MeV protons in a niobium target. To recover unconverted H$_2$$^{18}$O, the [$^{18}$F]-fluoride/H$_2$$^{18}$O solution was passed through a short plug of anion-exchange resin (~10 mg, CO$_3$$^{2-}$ form). Resin bound fluoride was eluted with 200 to 300 µL of 1 mg/mL NaClO$_4$ and recovered in a glass vial. Depending on the desired activity, this sample could be diluted with deionized water, used as is, or excess water could be removed through heating under vacuum.

Low-Activity Radiochemical Synthesis of the Trifluoroborate of [$^{18/19}$F]-(3) for Gel Electrophoresis and Isotopic Exchange.

1.95 mCi (t=0 min) of [$^{18}$F]-fluoride was prepared from the proton bombardment of H$_2$$^{18}$O. This sample was dried and bought up with 2 µl of 2M HCl to give a pH 3 solution. This solution was added to 1.5 µL of a 200 mM solution of (2) in DMF (300 nmols) before 0.2 µL of 4M [$^{19}$F]-KHF$_2$ was added (1600 nmols F$^-$)(t=16 min). The activity of this reaction mixture was 1 mCi (t=30 min) (Approximately 50% of activity was lost due to non-specific binding). The fluoridation reaction was allowed to proceed at room temperature for 159 min, after which the reaction was quenched with 50 µL of MeOH and placed over a Pasteur pipet packed with 600 mg of dry 230-400 mesh silica. [$^{18/19}$F]-(3) was eluted with 500 µL of a 95:5 EtOH:NH$_4$OH solution and had an activity of 22.7 µCi (t=184 min). A radiochemical yield of 15% (~75 nmols of [$^{18/19}$F]-(3)) was estimated from phosphorimaging analysis of the autoradiography of the crude reaction following TLC resolution. The purified fraction (~500 µL) was centrifuged in an Eppendorf Microcentrifuge 5415 C at 2000 rpm for 2 min and decanted from an SiO$_2$ pellet. This solution is heretofore called "Sample-A".

[$^{18}$F] Isotope Exchange—Using the Low-Activity Radiochemical Synthesis of [$^{18/19}$F]-(3).

In order to assay the dissociation rate of [$^{18}$F]-fluoride from the trifluoroborate (3), The six aliquots of Sample-A (each 10 µL, 1.5 nmol [$^{18/19}$F]-(3), 0.45 µCi (t=184 min)) were diluted 30 fold into 300 µL of a 200 mM PO$_4$, pH 7.5, 100 mM [$^{19}$F]—NaF solution at different times. A volume of 0.5 µL of each dilution was spotted on a TLC plate which is run 2 inches in a 5:95 NH$_4$OH:ethanol developing solution. Each spot that was deposited on the plate had spent increasing amounts of time in the solution containing a vast excess of [$^{19}$F]-fluoride. Following autoradiography, a rate constant for the isotopic exchange of [$^{18}$F]-fluoride from [$^{18/19}$F]-(3) was calculated. The half-life for the solvolysis of this ArBF$_3$$^-$ was minimally 3800 min. suggesting that 10% of the fluoride will be solvolytically liberated in a period not shorter than 833 min., or approximately 7.5 half-lives of $^{18}$F-decay Polyacrylamide Gel Electrophoresis Experiments—Using the Low-Activity Radiochemical Synthesis of [$^{18/19}$F]-(3).

400 µL of Sample-A, (60 nmol, 18.2 µCi (t=184 min)) was mixed with tetrameric NeutrAvidin™ (Pierce) in a 1:4 molar ratio of biotin:avidin, such that the final solution was 80% phosphate-buffered saline and 20% ethanol at room temperature for 45 min (the ethanol came from the NH$_4$OH:ethanol solution used in the preceding chromatography). One volume of non-denaturing sample buffer was added and differing amounts of sample were loaded onto a 12% SDS-PAGE gel run at 100 V (12 W). Following electrophoresis, this gel was transferred to Whatman filter paper and exposed to a phosphorimager screen. As a control, tetrameric NeutrAvidin™ was also incubated with fluorescent Biotin-Atto680™ (Sigma), loaded onto a 12% SDS-PAGE gel and visualized using a Licor Odyssey™ near infrared fluorescence gel scanner.

High-Activity Radiochemical Synthesis of the Trifluoroborate of [$^{18/19}$F]-(3) for In Vivo Imaging.

100 mCi (t=0 min) of [$^{18}$F]-fluoride was prepared from the proton bombardment of H$_2$$^{18}$O. This sample was dried and bought up with a solution of 1.75 µL of 2M HCl and 1 µL of 0.4 M KHF$_2$ to give a volume of 2.75 µL of a solution (pH of –3) containing 800 nmols of [$^{18/19}$F]-fluoride with a specific activity of 0.126 Ci/µmol (t=0 min) at a concentration of 291 mM. This solution was added to 1 µL of a 200 mM solution of (2) in DMF (t=4 min) to give a total volume of 3.75 µL reaction solution that was 53 mM in Boron, 213 mM in [$^{18/19}$F]-fluoride, and 100 mCi (t=40 min). The remainder of activity was apparently lost due to non-specific binding and evaporation. This reaction was heated in a closed 600 µL eppendorf tube for 160 min at 41° C., after which it was quenched with 30 µL of 95:5 EtOH/NH$_4$OH (t=160 min) and eluted through a Pasteur pipet packed with 600 mg of dry 230-400 mesh silica. Five 100 µL fractions were collected using 95:5 EtOH/NH$_4$OH as the eluant. The first two fractions containing the majority of [$^{18/19}$F]-(3) were pooled and concentrated to 150 µL. In this pooled fraction, 2-2.3 mCi of [$^{18/19}$F]-(3) was obtained at t=160 min, with a decay-corrected specific activity of 0.12 Ci/µmol, or 18 nmol of [$^{18/19}$F]-(3) corresponding to a chemical yield of 9% with respect to boron. This solution is heretofore referred to as "Sample-B" and was taken to be 120 □µM in labeled biotin. A volume of 10 µL of Sample-B was added directly to 190 µL of phosphate buffered saline (pH 7.5) and transferred to the UBC hospital for tail vein injection. To image [$^{18}$F]-labeled NeutrAvidin™, 10 µL of Sample-B corresponding to 2-2.3 mCi of [$^{18/19}$F]-(3), (t=160 min) and (1.2 nmol 3) were added to 90 µL of phosphate buffered saline and 100 µL of 2 mg/mL NeutrAvidin™ (125 µM in monomeric avidin, or 12.5 nmol monomeric avidin). 150 µl (100 µCi, t=194 min) of this sample was used for mouse tail vein injection.

Figure 5:
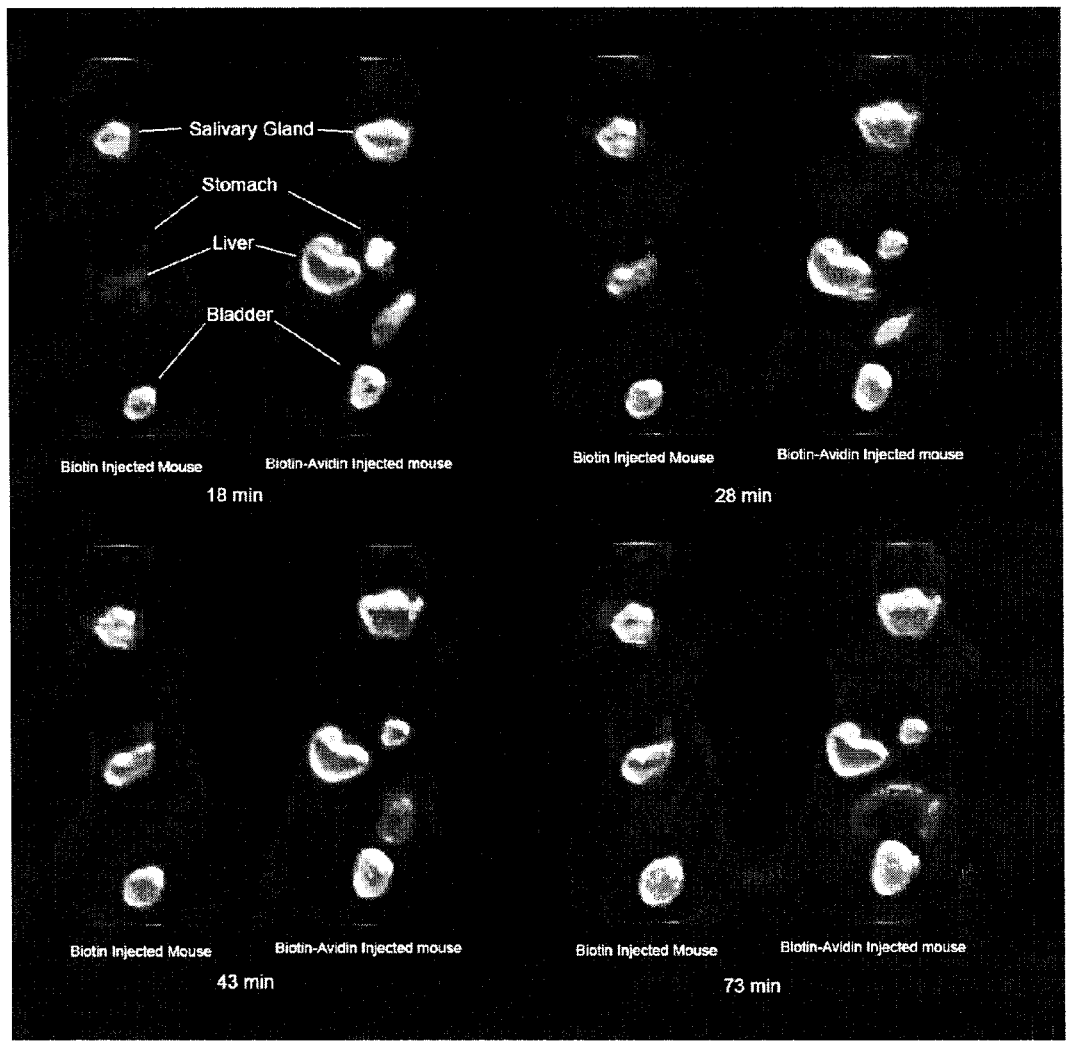
FIG. 5: are PET scans of mice showing distribution of $^{18}$F labeled biotin and $^{18}$F labeled biotin-NeutrAvidin™ over time.

In Vivo Biodistribution:

Two 10 week old female Balb/c mice were injected via the tail vein with ~127 and 100 µCi of either [$^{18/19}$F]-(3) or [$^{18/19}$F]-(3) preincubated with NeutrAvidin™, respectively (t=194 min). After injection the animals were anaesthetized with isofluorane (5% induction, 1.5% maintenance) and subjected to a 90 min dynamic scan followed by a 10 min transmission scan. There was a 13 minute delay between each injection with the first mouse receiving [$^{18/19}$F]-(3) alone and the second mouse receiving the NeutrAvidin™-complexed [$^{18/19}$F]-(3). PET data were compiled with Siemens Focus120™ microPET software. PET images (FIG. 5) were generated with the open source program, Amide© version 0.8.19.

While specific embodiments of the invention have been described and illustrated, such embodiments should be considered illustrative of the invention only and not as limiting the invention. All published documents and patent documents referred to herein are incorporated by reference.

The invention claimed is:

1. A positron emitting compound or salt thereof, wherein the compound has the formula:

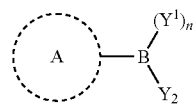

wherein:

B is boron;

A is a single substituted aromatic ring or an aromatic ring joined to one or more additional rings to form a substituted polycyclic moiety, wherein ring atoms comprise carbon and optionally, one or more heteroatoms, and substituents of the aromatic ring or polycyclic moiety other than B comprise at least one electron-withdrawing group (EWG);

each $(Y^1)_n$ is independently selected from the group consisting of $R^1$, $^{18}F$ and $^{19}F$, and n=1 or 2;

$Y^2$ is selected from the group consisting of $R^1$, $^{18}F$ and $^{19}F$;

$R^1$ is a non-interfering substituent with regard to fluorination of B;

providing that at least one of $(Y^1)_n$ and $Y^2$ is $^{18}F$;

providing that $\sigma_{total}$ for all substituents on the aromatic ring or polycyclic moiety except B is about 0.06 or more when said at least one EWG is positioned ortho to B, or about 0.2 or more when no EWG is positioned ortho to B;

and providing that said at least one EWG is not a single bromomethyl group positioned ortho to B.

2. The compound or salt of claim 1, wherein the compound has the formula:

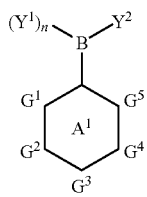

wherein:

$A^1$ is the aromatic ring and $G^{1-5}$ are independently substituted or unsubstituted C or N;

$G^1$ with $G^2$, $G^2$ with $G^3$, $G^3$ with $G^4$ or $G^4$ with $G^5$ optionally join with substituents thereof to form one or two additional rings of said polycyclic moiety;

and wherein at least one of $G^{1-5}$ or at least one of said additional ring or rings is substituted by said at least one EWG.

3. The compound or salt of claim 2, wherein at least one EWG is positioned ortho to B.

4. The compound or salt of claim 3, wherein $\sigma_{total}$ is about 0.2 or more.

5. The compound or salt of claim 2, wherein two EWG's are positioned ortho to B.

6. The compound or salt of claim 2, wherein at least one EWG is positioned meta or para to B or both meta and para to B.

7. The compound or salt of claim 6, wherein $\sigma_{total}$ is about 0.8 or more.

8. The compound or salt of claim 2, wherein at least one EWG is positioned ortho to B, at least one EWG is positioned meta or para to B or both meta and para to B, and no group that anchimerically assists de-fluorination at B is positioned ortho to B.

9. The compound or salt of claim 8, wherein $\sigma_{total}$ is about 0.2 or more.

10. The compound or salt of claim 2, having a de-18-fluorination half-life of about 1000 minutes or more.

11. The compound or salt of claim 2, wherein at least one of $G^{1-5}$ is independently substituted or unsubstituted N.

12. The compound or salt of claim 2, wherein $G^{1-5}$ are independently substituted or unsubstituted C.

13. The compound or salt of claim 2, wherein:

at least one EWG is positioned ortho to B, and no group that anchimerically assists de-fluorination at B is positioned ortho to B;

$\sigma_{total}$ is about 0.2 or more;

n=2;

each $(Y^1)_n$ is independently selected from the group consisting of $^{18}F$ and $^{19}F$;

$Y^2$ is selected from the group consisting of $^{18}F$ and $^{19}F$; and $A^1$ is further substituted with a linking group, a biomolecule or a linking group joined to a biomolecule.

14. The compound or salt of claim 13, wherein $A^1$ is further substituted with a biomolecule or a linking group joined to a biomolecule and the biomolecule comprises an enzyme inhibitor, a vitamin, a peptide, an oligonucleotide, a hormone, an antibody or a derivative or analog thereof.

15. The compound or salt of claim 2, wherein:

at least one EWG is positioned meta or para to B or both meta and para to B;

$\sigma_{total}$ is about 0.8 or more;

n=2;

each $(Y^1)_n$ is independently selected from the group consisting of $^{18}F$ and $^{19}F$;

$Y^2$ is selected from the group consisting of $^{18}F$ and $^{19}F$; and $A^1$ is further substituted with a linking group, a biomolecule or a linking group joined to a biomolecule.

16. The compound or salt of claim 15, wherein $A^1$ is further substituted with a biomolecule or a linking group joined to a biomolecule and the biomolecule comprises an enzyme inhibitor, a vitamin, a peptide, an oligonucleotide, a hormone, an antibody or a derivative or analog thereof.

17. The compound or salt of claim 2, wherein:

at least one EWG is positioned ortho to B;

at least one EWG is positioned meta or para to B or both meta and para to B;

no group that anchimerically assists de-fluorination at B is positioned ortho to B;

$\sigma_{total}$ is about 0.2 or more;

n=2;

each $(Y^1)_n$ is independently selected from the group consisting of $^{18}F$ and $^{19}F$;

$Y^2$ is selected from the group consisting of $^{18}F$ and $^{19}F$; and $A^1$ is further substituted with a linking group, a biomolecule or a linking group joined to a biomolecule.

18. The compound or salt of claim 17, wherein $A^1$ is further substituted with a biomolecule or a linking group joined to a biomolecule and the biomolecule comprises an enzyme inhibitor, a vitamin, a peptide, an oligonucleotide, a hormone, an antibody or a derivative or analog thereof.

19. The compound or salt of claim 1, wherein an EWG is positioned ortho to B.

20. The compound or salt of claim 19, wherein $\sigma_{total}$ is about 0.12 or more.

21. The compound or salt of claim 19, wherein $\sigma_{total}$ is about 0.15 or more.

22. The compound or salt of claim 19, wherein $\sigma_{total}$ is about 0.2 or more.

23. The compound or salt of claim 1, wherein two EWG's are positioned ortho to B.

24. The compound or salt of claim 1, wherein an EWG is positioned meta or para to B or both.

25. The compound or salt of claim 1, wherein $\sigma_{total}$ is about 0.35 or more.

26. The compound or salt of claim 1, wherein $\sigma_{total}$ is about 0.6 or more.

27. The compound or salt of claim 1, wherein $\sigma_{total}$ is about 0.8 or more.

28. The compound or salt of claim 1, wherein $\sigma_{total}$ is about 1.0 or more.

29. The compound or salt of claim 1, wherein no group that anchimerically assists de-fluorination at B is positioned ortho to B.

30. The compound or salt of claim 1, having a de-18-fluorination half-life of about 30 minutes or more.

31. The compound or salt of claim 1, having a de-18-fluorination half-life of about 60 minutes or more.

32. The compound or salt of claim 1, having a de-18-fluorination half-life of about 120 minutes or more.

33. The compound or salt of claim 1, having a de-18-fluorination half-life of about 180 minutes or more.

34. The compound or salt of claim 1, having a de-18-fluorination half-life of about 300 minutes or more.

35. The compound or salt of claim 1, wherein A is further substituted with a linking group.

36. The compound or salt of claim 1, wherein A is further substituted with a biomolecule.

37. The compound or salt of claim 36, wherein the biomolecule comprises an enzyme inhibitor, a vitamin, a peptide, an oligonucleotide, a hormone, an antibody or a derivative or analog thereof.

38. A trifluoroborate compound or salt of claim 1.

39. The compound or salt of claim 1, wherein at least one EWG is positioned ortho to B and no group that anchimerically assists de-fluorination at B is positioned ortho to B.

40. The compound or salt of claim 39, wherein:
A is further substituted with a linking group, a biomolecule or a linking group joined to a biomolecule;
n=2;
each $(Y^1)_n$ is independently selected from the group consisting of $^{18}F$ and $^{19}F$; and
$Y^2$ is selected from the group consisting of $^{18}F$ and $^{19}F$.

41. The compound or salt of claim 1, wherein at least one EWG is positioned ortho to B, at least one EWG is positioned meta or para to B or both meta and para to B, and no group that anchimerically assists de-fluorination at B is positioned ortho to B.

42. The compound or salt of claim 41, wherein:
A is further substituted with a linking group, a biomolecule or a linking group joined to a biomolecule;
n=2;
each $(Y^1)_n$ is independently selected from the group consisting of $^{18}F$ and $^{19}F$; and
$Y^2$ is selected from the group consisting of $^{18}F$ and $^{19}F$.

* * * * *